United States Patent
Jalgaonkar et al.

(10) Patent No.: US 11,633,193 B2
(45) Date of Patent: Apr. 25, 2023

(54) EXPANDABLE DEVICES AND ASSOCIATED SYSTEMS AND METHODS

(71) Applicant: Covidien LP, Mansfield, MA (US)

(72) Inventors: Ujwal Jalgaonkar, Irvine, CA (US);
Eric Mintz, Newport Coast, CA (US);
Gaurav Girdhar, Ladera Ranch, CA (US); John Wainwright, Irvine, CA (US); Ashok Nageswaran, Irvine, CA (US); Minh Dinh, Fremont, CA (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 16/948,127

(22) Filed: Sep. 3, 2020

(65) Prior Publication Data
US 2022/0061854 A1  Mar. 3, 2022

(51) Int. Cl.
*A61F 2/86* (2013.01)
*A61B 17/12* (2006.01)
*A61F 2/06* (2013.01)

(52) U.S. Cl.
CPC .. *A61B 17/12168* (2013.01); *A61B 17/12109* (2013.01); *A61B 17/12113* (2013.01); *A61F 2/86* (2013.01); *A61F 2002/065* (2013.01); *A61F 2002/068* (2013.01); *A61F 2210/0014* (2013.01); *A61F 2250/0006* (2013.01); *A61F 2250/0098* (2013.01)

(58) Field of Classification Search
CPC ........ A61B 17/12168; A61B 17/12109; A61B 17/12113; A61F 2/86; A61F 2/06; A61F 2/07; A61F 2002/065; A61F 2002/061; A61F 2002/068; A61F 2250/0006; A61F 2250/0098; A61F 2210/0014
See application file for complete search history.

(56) References Cited

U.S. PATENT DOCUMENTS

| | | | | |
|---|---|---|---|---|
| 5,674,241 | A * | 10/1997 | Bley | A61F 2/07 606/198 |
| 6,682,557 | B1 * | 1/2004 | Quiachon | A61F 2/954 623/1.36 |
| 10,342,686 | B2 | 7/2019 | Choubey | |
| 2004/0138736 | A1 | 7/2004 | Obara | |
| 2004/0158311 | A1 | 8/2004 | Berhow et al. | |
| 2006/0116748 | A1 * | 6/2006 | Kaplan | A61F 2/856 623/1.11 |
| 2011/0046720 | A1 | 2/2011 | Shalev et al. | |

(Continued)

FOREIGN PATENT DOCUMENTS

WO  2013009976 A2  1/2013

OTHER PUBLICATIONS

Extended European Search Report dated Feb. 8, 2022; European Application No. 21193581.2; 7 pages.

*Primary Examiner* — Dinah Baria
(74) *Attorney, Agent, or Firm* — Fortem IP LLP; Katrina Marcelo; Matthew Lincicum

(57) ABSTRACT

Expandable devices are disclosed herein. Several of the embodiments are directed towards an expandable device comprising a mesh configured to be expanded at a blood vessel bifurcation of a human patient. The mesh may comprise a tubular body portion and one or more circumferentially discontinuous articulating portions. The mesh may be expanded such that the one or more articulating portions are positioned at an angle to the tubular body portion.

23 Claims, 10 Drawing Sheets

(56) References Cited

U.S. PATENT DOCUMENTS

| | | |
|---|---|---|
| 2017/0273692 A1 | 9/2017 | Choubey |
| 2017/0273810 A1 | 9/2017 | Choubey et al. |
| 2019/0133795 A1 | 5/2019 | Choubey |
| 2019/0192322 A1 | 6/2019 | Choubey et al. |
| 2019/0223879 A1* | 7/2019 | Jayaraman ............... A61F 2/90 |
| 2019/0269534 A1 | 9/2019 | Choubey |
| 2019/0314175 A1 | 10/2019 | Dawson et al. |
| 2019/0314176 A1 | 10/2019 | Nageswaran et al. |
| 2019/0314177 A1 | 10/2019 | Monso et al. |
| 2019/0314179 A1 | 10/2019 | Nageswaran et al. |
| 2019/0380852 A1 | 12/2019 | Eker et al. |

* cited by examiner

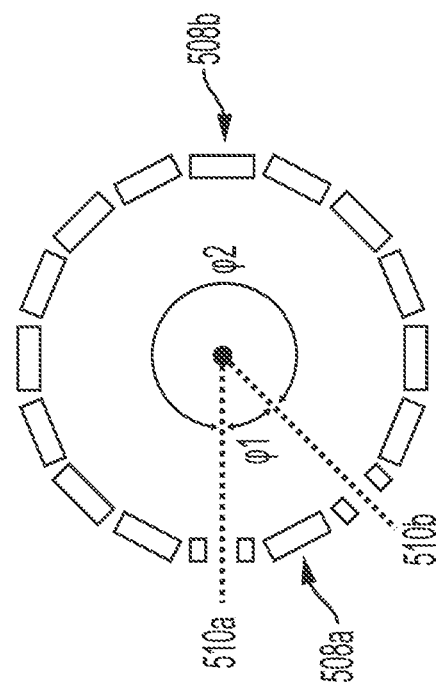
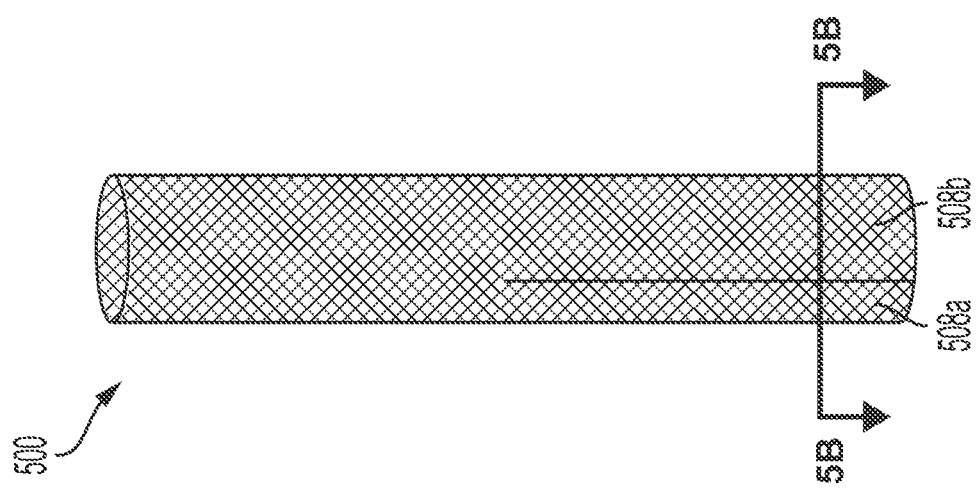

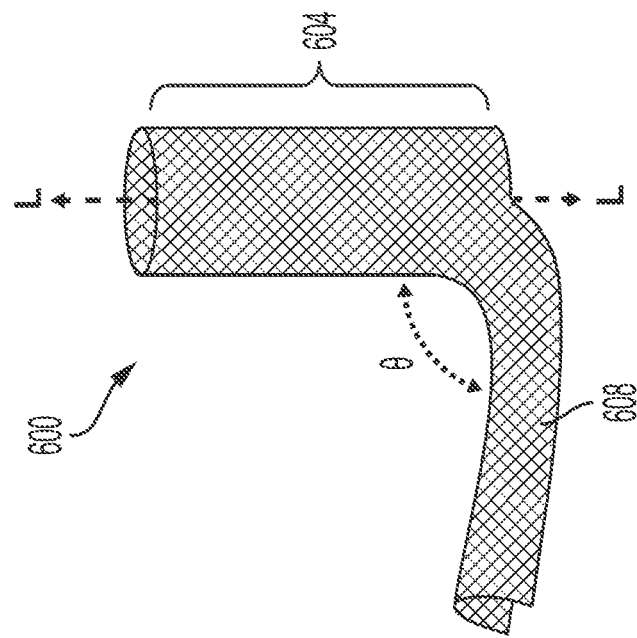
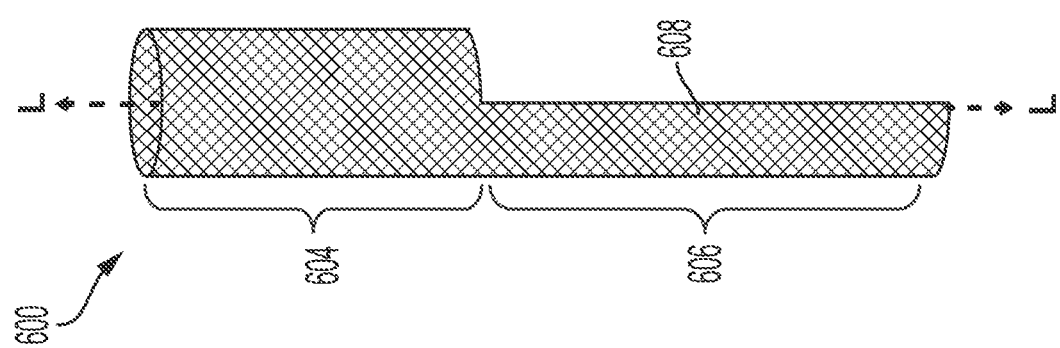

EXPANDABLE DEVICES AND ASSOCIATED SYSTEMS AND METHODS

TECHNICAL FIELD

The present technology relates to expandable devices and associated systems and methods. In particular embodiments, the present technology relates to devices for diverting blood flow in in a blood vessel. In some embodiments, the present technology relates to devices for preventing blood flow into an aneurysm at a bifurcation of a blood vessel, and associated systems and methods of use.

BACKGROUND

Aneurysms are an abnormal bulging or ballooning of a blood vessel that can result from the vessel wall being weakened by disease, injury, or a congenital abnormality. Aneurysms have thin, weak walls and a tendency to rupture, which can lead to stroke, death, disability, etc. Aneurysms may be treated by positioning an occlusive device (e.g., coils, braids, liquid embolics, etc.) within the aneurysm to reduce blood flow and promote thrombosis and embolization within the aneurysm. However, intrasaccular occlusive devices may relocate out of the aneurysm and into the vessel with aneurysms with wide necks, which may lead to arterial occlusion, stroke, and/or death.

Another method of treating aneurysms includes inserting a flow-diverting stent or braid into a parent vessel that includes the aneurysm to be treated. Such stents or braids can be inserted into a vessel in a radially constrained state, positioned next to the neck of the aneurysm, and expanded into apposition with the vessel wall. If the stent or braid has a sufficiently low porosity, it can function to block the flow of blood through the device and into the aneurysm to induce embolization of the aneurysm. A flow-diverting device may be placed within two vessels (e.g., a parent vessel and a first branching vessel, a first branching vessel and a second branching vessel) to treat a bifurcation aneurysm between the vessels. However, flow-diverting devices typically comprise a tubular structure. Consequently, when such flow-diverting devices are placed across the neck of the aneurysm, a portion of the device is positioned across a juncture to another blood vessel and disrupts blood flow to the vessel. Accordingly, there exists a need for improved flow-diverting devices for treating bifurcation aneurysms.

SUMMARY

The present technology is directed to devices for treating bifurcation aneurysms and associated systems and methods. According to some embodiments, the expandable devices of the present technology comprise an expandable mesh having circumferentially discontinuous articulating portions configured to be positioned at an angle with respect to a tubular body portion of the mesh when the device is expanded. The expandable devices of the present technology may be particularly beneficial for treating bifurcation aneurysms at a location in which a parent blood vessel branches into two or more branching vessels. For example, the expandable meshes of the present technology may be configured to be positioned adjacent the bifurcation aneurysm such that the tubular body portion of the mesh is positioned within a first branching vessel, one of the articulating portions is positioned within a second branching vessel, and another one of the articulating portions is positioned within a parent vessel such that one or more portions of the expandable mesh is positioned across a neck of the bifurcation aneurysm and prevents blood flow into the aneurysm.

The subject technology is illustrated, for example, according to various aspects described below, including with reference to FIGS. 1A-10. Various examples of aspects of the subject technology are described as numbered clauses (1, 2, 3, etc.) for convenience. These are provided as examples and do not limit the subject technology.

Clause 1. An expandable device configured to be positioned across a neck of an aneurysm at a bifurcation of a blood vessel of a patient, the device comprising:
 a generally tubular mesh having a first end portion and a second end portion, the second end portion comprising a first articulating region and a second articulating region,
 wherein the first articulating region is separated from the second articulating region by first and second slits, the first and second slits extending along a longitudinal axis of the mesh, and
 wherein, when the mesh is in an expanded state, the first articulating region is positioned at a first angle relative to the first end portion and the second articulating region is positioned at a second angle relative to the first end portion.

Clause 2. The device of Clause 1, wherein a length of the first slit is equal to a length of the second slit.

Clause 3. The device of Clause 1 or Clause 2, wherein the first slit is circumferentially spaced apart from the second slit by about 180 degrees.

Clause 4. The device of Clause 1 or Clause 2, wherein a width of the first articulating region is less than a width of the second articulating region.

Clause 5. The device of any one of Clause 1 to Clause 4, wherein the first angle is about 0 degrees and the second angle is between about 30 degrees and 150 degrees.

Clause 6. The device of any one of Clause 1 to Clause 4, wherein the first angle is substantially equivalent to the second angle.

Clause 7. The device of any one of Clause 1 to Clause 6, wherein the first and second slits are formed by mechanical or laser cutting.

Clause 8. The device of any one of Clause 1 to Clause 7, wherein longitudinal edges of the first and second articulating regions adjacent first and second slits have been soldered, melted, welded, or glued.

Clause 9. The device of any one of Clause 1 to Clause 8, the mesh further comprising a third slit extending circumferentially between the first slit and the second slit.

Clause 10. The device of any one of Clause 1 to Clause 9, further comprising a plurality of radiopaque markers positioned around a circumference of the first end portion of the mesh.

Clause 11. The device of any one of Clause 1 to Clause 10, further comprising a first plurality of radiopaque markers attached to the first articulating region and a second plurality of radiopaque makers attached to the second articulating region.

Clause 12. The device of Clause 11, wherein the first plurality of radiopaque markers comprises fewer radiopaque markers than the second plurality of radiopaque markers.

Clause 13. A device configured to be positioned across a neck of an aneurysm at a bifurcation of a blood vessel of a patient, the device comprising:
 an expandable mesh having a generally tubular body portion and a circumferentially discontinuous arm portion extending from the body portion, wherein, when the expandable mesh is in a low-profile configuration, a longitudinal axis of the arm portion is generally parallel with a longitudinal axis of the body portion, and wherein, when the expandable mesh is in an expanded configuration, a longitudinal axis of the arm portion is positioned at an angle with respect to the longitudinal axis of the body portion.

Clause 14. The device of Clause 13, wherein the angle is between about 30 degrees and about 150 degrees Clause 15. The device of Clause 13 or Clause 14, wherein the body portion is configured to be positioned within a first blood vessel and the arm portion is configured to be placed within a second blood vessel.

Clause 16. The device of any one of Clause 13 to Clause 15, wherein the arm portion is a first arm portion, the mesh further comprising a second arm portion extending from the body portion, wherein, when the expandable mesh is in an expanded configuration, a longitudinal axis of the first arm portion is positioned at a first angle to the longitudinal axis of the body portion and a longitudinal axis of the second arm portion is positioned at a second angle to the longitudinal axis of the body portion.

Clause 17. The device of any one of Clause 13 to Clause 16, wherein the mesh is configured to divert blood flow away from the aneurysm.

Clause 18. The device of any one of Clause 13 to Clause 17, wherein the mesh comprises a braid.

Clause 19. The device of any one of Clause 13 to Clause 18, wherein the mesh is self-expanding.

Clause 20. The device of any one of Clause 13 to Clause 19, wherein the mesh is formed of a shape memory alloy.

Clause 21. The device of any one of Clause 16 to Clause 20, wherein the body portion is configured to be positioned within a first branching blood vessel, the first arm portion is configured to be placed within a second branching blood vessel, and the second arm portion is configured to be placed within a parent blood vessel.

Clause 22. The device of any one of Clause 13 to Clause 21, wherein the mesh is configured to anchor to a wall of the blood vessel of the patient.

Clause 23. A device for reducing blood flow within an aneurysm of a blood vessel, the device comprising:
an expandable mesh comprising a circumferentially discontinuous first portion, a circumferentially discontinuous second portion, and a generally tubular third portion, the expandable device having a radially constrained configuration and an expanded configuration,
wherein, when the expandable mesh is in the radially constrained configuration the device comprises a substantially tubular shape,
wherein, when the expandable mesh is in the expanded configuration, the first portion is configured to be positioned within a parent blood vessel, the second portion is configured to be positioned within a first branching blood vessel, and the third portion is configured to be positioned within a second branching blood vessel, and
wherein, when positioned across a neck of the aneurysm, the device is configured to substantially block blood flow into the aneurysm and permit blood flow from the parent blood vessel to the first and second branching blood vessels.

Clause 24. The device of Clause 23, wherein the second and third portions are configured to substantially cover the neck of the aneurysm.

Clause 25. The device of Clause 23, wherein the first and third portions are configured to substantially cover the neck of the aneurysm.

Clause 26. The device of Clause 23, wherein the first and second portions are configured to substantially cover the neck of the aneurysm.

Clause 27. A device for reducing blood flow within an aneurysm of a blood vessel, the device comprising:
an expandable mesh comprising a first portion, a second portion, and a third portion, wherein at least one of the portions is circumferentially discontinuous, the expandable device having a radially constrained configuration and an expanded configuration,
wherein, when the expandable mesh is in the radially constrained configuration the device comprises a substantially tubular shape,
wherein, when the expandable mesh is in the expanded configuration, the first portion is configured to be positioned within a parent blood vessel, the second portion is configured to be positioned within a first branching blood vessel, and the third portion is configured to be positioned within a second branching blood vessel, and
wherein, when positioned across the neck of the aneurysm, the device is configured to substantially block blood flow into the aneurysm and permit blood flow from the parent blood vessel to the first and second branching blood vessels.

Clause 28. The device of Clause 27, wherein the third portion is substantially tubular and the first and second portions are circumferentially discontinuous.

Clause 29. The device of Clause 27, wherein the first and third portions are substantially tubular and the second portion is circumferentially discontinuous.

Clause 30. The device of any one of Clause 27 to Clause 29, wherein the at least one of the portions subtends an angle of about 30 degrees to about 330 degrees.

Clause 31. The device of any one of Clause 27 to Clause 29, wherein the at least one of the portions subtends an angle of about 180 degrees.

Clause 32. A method of making an expandable device comprising:
obtaining a tubular mesh having a porosity configured to divert blood flow, the tubular mesh comprising a first end portion, a second end portion, and an intermediate portion therebetween;
forming a circumferentially discontinuous arm portion from the second end portion of the tubular mesh, the arm portion being movable relative to the first end portion of the mesh;
manipulating the mesh into an expanded configuration; and
shape-setting the mesh in the expanded configuration.

Clause 33. The method of Clause 32, wherein forming the arm portion comprises creating at least two slits in the tubular mesh.

Clause 34. The method of Clause 32 or Clause 33, wherein manipulating the mesh into an expanded configuration comprises obtaining a fixture and coupling the mesh to the fixture.

Clause 35. The method of any one of Clause 32 to Clause 34, wherein shape setting the mesh into an expanded configuration comprises heat treating the mesh.

Clause 36. The method of any one of Clause 33 to Clause 35, wherein creating the at least two slits comprises laser cutting the tubular mesh.

Clause 37. The method any one of Clause 33 to Clause 36, wherein the first end portion is a proximal end portion, the second end portion is a distal end portion, and each of the at least two slits extends proximally from a distal terminus of the distal end portion along a longitudinal axis of the device.

Clause 38. The method of any one of Clause 33 to Clause 36, wherein each of the at least two slits extends along a longitudinal axis of the device within the intermediate portion.

Clause 39. The method of any one of Clause 33 to Clause 38 wherein the arm portion is a first arm portion, the method further comprising forming a second arm portion.

Clause 40. An expandable device delivery system comprising:
- a core member configured for advancement within a corporeal lumen, the core member comprising a distal portion, a first proximal portion, and a second proximal portion, the first and second proximal portions being radially spaced apart;
- a first pushing element fixed to the first proximal portion of the core member and a second pushing element fixed to the second proximal portion of the core member, wherein each of the first and second pushing elements comprises a distal-facing engagement surface;
- an orientation member coupled to the first proximal portion of the core member, the orientation member configured to rotate the first proximal portion of the core member; and
- an expandable device comprising a distal end portion and two arm portions extending proximally from the distal end portion, wherein each of the two arm portions comprises a proximal edge,
- wherein the distal-facing engagement surface the first pushing element abuts the proximal edge of the first arm portion and the distal-facing engagement surface of the second pushing element abuts the proximal edge of the second arm portion.

Clause 41. The system of Clause 40, wherein the first and second pushing elements are configured to transmit distally directed force to the expandable device.

Clause 42. The system of Clause 40 or Clause 41, further comprising a plate rotatably positioned about the core member.

Clause 43. The system of Clause 42, wherein the plate is configured to transmit proximally or radially outwardly directed force to the expandable device.

Clause 44. The system of any one of Clause 40 to Clause 43, further comprising a sheath or catheter, wherein the core member, first and second pushing elements, and the expandable device are located within a lumen of the sheath or catheter.

Clause 45. The system of any one of Clause 40 to Clause 44, wherein each of the first and second pushing elements comprises a proximal restraining member.

Clause 46. The system of any one of Clause 40 to Clause 46, further comprising a distal restraining member coupled to the core member.

Clause 47. The system of any one of Clause 40 to Clause 46, wherein the orientation member is rotatably positioned about the second proximal portion of the core member.

Clause 48. A method of treating an aneurysm positioned between a first blood vessel and a second blood vessel at a blood vessel bifurcation comprising the first blood vessel, the second blood vessel, and a third blood vessel, the method comprising:

providing an expandable device for diverting blood flow away from an aneurysm, the expandable device comprising:
- an expandable mesh comprising a plurality of arm portions, the plurality of arm portions including a first arm portion, a second arm portion, and a third arm portion, wherein at least one of the plurality of portions is circumferentially discontinuous, the expandable mesh having a generally tubular radially constrained state for delivery within a microcatheter, and an expanded state in which the second arm portion is positioned at a first angle to a longitudinal axis of the first arm portion and the third arm portion is positioned at a second angle to a longitudinal axis of the first arm portion;
- advancing the first arm portion of the expandable device into to the first blood vessel and expanding the first arm portion into contact with a wall of the first blood vessel; and
- advancing the second arm portion into the second blood vessel and expanding the second arm portion into contact with at least a portion of a wall of the second branching blood vessel such that at least a portion of the second arm portion is positioned across a neck of the aneurysm; and
- expanding the third arm portion into contact with at least a portion of a wall of the third blood vessel.

Clause 49. The method of Clause 48, wherein the first arm portion is circumferentially continuous.

Clause 50. The method of Clause 48 or Clause 49, wherein the second arm portion is circumferentially discontinuous.

Clause 51. The method of any one of Clause 48 to Clause 50, wherein at least a portion of the third arm portion is circumferentially discontinuous.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

FIG. 5A is an isometric view of an expandable device configured in accordance with embodiments of the present technology.

FIG. 5B is an axial cross-sectional view of the expandable device shown in FIG. 5A taken along line 5B-5B.

FIGS. 6A and 6B are isometric views of an expandable device configured in accordance with embodiments of the present technology, shown in a tubular configuration and an expanded configuration, respectively.

DETAILED DESCRIPTION

Figure 1A:
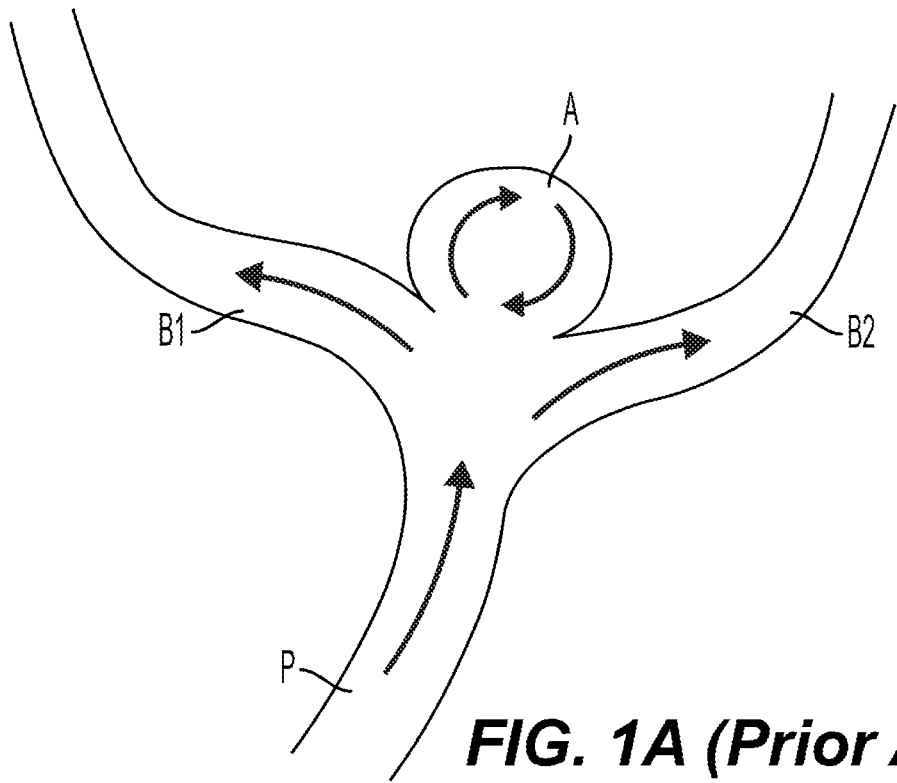
FIG. 1A depicts an example bifurcation aneurysm located between two branching blood vessels at a bifurcation of a parent blood vessel.

The present technology relates to expandable devices and associated systems and methods. Some embodiments of the present technology, for example, are directed to flow-diverting expandable meshes configured to be positioned within one or more blood vessels at a blood vessel bifurcation and across a neck of a bifurcation aneurysm. Specific details of several embodiments of the technology are described below with reference to FIGS. 1A-10.

With regard to the terms "distal" and "proximal" within this description, unless otherwise specified, the terms can reference a relative position of the portions of an interventional device such as a flow-diverting device and/or an associated delivery device with reference to an operator and/or a location in the vasculature. For example, in referring to a delivery system including the expandable flow-diverting devices described herein, "proximal" can refer to a position closer to the operator of the device or an incision into the vasculature, and "distal" can refer to a position that is more distant from the operator of the device or further from the incision along the vasculature (e.g., the end of the catheter).

As used herein, "radially constrained configuration" refers to an unexpanded configuration of the expandable device in which the expandable device is configured to be delivered or withdrawn through a catheter to or from a treatment site. As used herein, "expanded configuration" refers to a configuration of the expandable device in which the expandable device is partially or fully expanded. An expanded configuration may be achieved via actuation only (for example, via inflation of a balloon), via self-expansion only, or both. Unless provided otherwise herein, "fully expanded," as used to describe a configuration of the expandable device, refers to a configuration of the expandable device in which the portions of the expandable device are positioned relative to the other portions of the expandable device as desired for treatment or facilitating treatment. For example, the fully expanded configuration of the expandable device may comprise an articulating portion of the expandable device positioned at an angle to a tubular body portion of the expandable device such that the articulating portion is configured to be positioned within a lumen of a branching vessel and across a neck of a bifurcation aneurysm and the tubular body portion is configured to be positioned within a lumen of a second branching vessel. As used herein, "intermediate expanded configuration" refers to a configuration of the expandable device in between the radially constrained configuration and the fully expanded configuration.

As used herein, the term "longitudinal" refers to a direction along an axis that extends through the lumen of the expandable device and/or stent while in a tubular configuration and the term "circumferential" can refer to a direction within a plane that is orthogonal to the longitudinal axis and extends around the circumference of the device when in a tubular configuration. As used herein, "circumferentially continuous" can refer to a portion of the device that has a closed circumference such that an axial cross-sectional shape of the device is a complete circle. As used herein, "circumferentially discontinuous" can refer to a portion of the device that has an open circumference such that an axial cross-sectional shape of the device is an arc that subtends an angle less than 360 degrees.

As used herein, "vessel bifurcation" refers to a location at which a parent blood vessel branches into two or more branching blood vessels. A bifurcation aneurysm refers to an aneurysm positioned between two branching blood vessels or between a parent blood vessel and a branching blood vessel.

As used herein, the terms "generally," "substantially," "about," and similar terms are used as terms of approximation and not as terms of degree, and are intended to account for the inherent variations in measured or calculated values that would be recognized by those of ordinary skill in the art.

Devices of the present technology may be configured to treat bifurcation aneurysms located at a bifurcation in a patient's vasculature in which a parent blood vessel P splits into two or more branching blood vessels B1, B2 (e.g., the aneurysm A illustrated in FIG. 1A). Compared to the bifurcation depicted in FIG. 1A, the branching vessels of the bifurcation may be at substantially different angles, have substantially different sizes, and/or be a different quantity (e.g., three or more). The aneurysm A of the bifurcation may be offset with respect to the junction (e.g., having a neck substantially open to one branching vessel), tilted with respect to a plane created by the vessels (e.g., into or out of the page), etc. Fluid flow into the aneurysm can cause the aneurysm A to rupture, which can lead to stroke, death, disability, etc. Consequently, it may be advantageous to treat the aneurysm to reduce blood flow into the aneurysm and, thereby, reduce the risk of adverse outcomes.

Figure 1B:
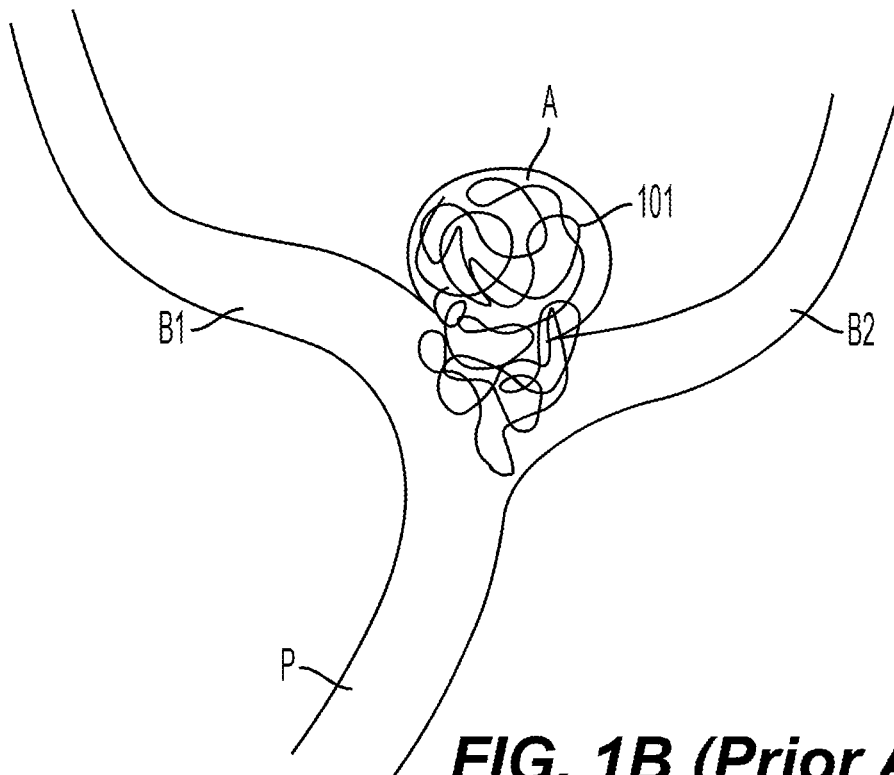
FIG. 1B depicts coil herniation from the example bifurcation aneurysm of FIG. 1A.

Intrasaccular occlusive devices such as, but not limited to, embolization coils 101 may be used to treat the aneurysm A. However, if the aneurysm A has a wide neck, the aneurysm A may be difficult to treat with an intrasaccular device (e.g., embolization coils 101) alone because the intrasaccular device may be prone to relocating through the aneurysm neck into the parent vessel, as illustrated in FIG. 1B. Relocation or herniation of the coils may cause arterial occlusion, stroke, and/or death. Flow-diverting devices may be used alone or in conjunction with intrasaccular devices to prevent blood flow into the aneurysm. However, tubular flow-diversion devices may insufficiently cover the neck of the aneurysm and may undesirably block blood flow into one of the vessels at the bifurcation. Thus, one or more devices, systems, and methods of the present technology are directed towards flow-diverting devices configured be positioned across a bifurcation aneurysm to prevent blood flow into the aneurysm while permitting blood flow from a parent vessel into two or more branching vessels.

Figure 2B:
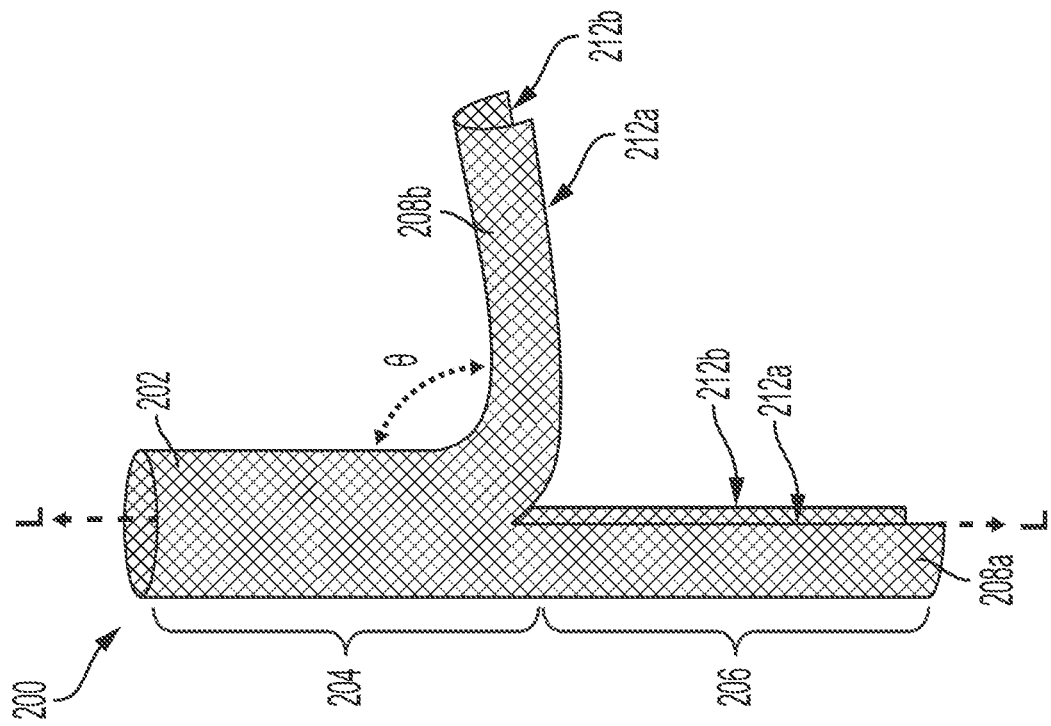
FIG. 2B is an isometric view of the expandable device shown in FIG. 2A in an expanded configuration configured in accordance with embodiments of the present technology.
Figure 2A:
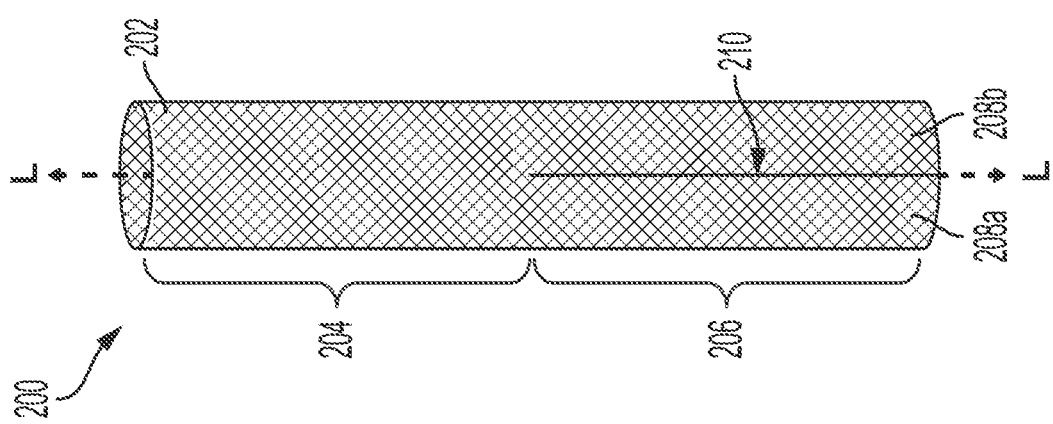
FIG. 2A is an isometric view of an expandable device in a tubular configuration configured in accordance with embodiments of the present technology.

FIGS. 2A and 2B are isometric views of an expandable, flow-diverting device ("device 200") configured in accordance with the present technology. The device 200 can comprise an expandable, flow-diverting mesh ("mesh 202") configured to interfere with blood flow to a degree sufficient to lead to thrombosis of the aneurysm. For example, the mesh 202 may have a sufficiently low porosity to prevent or reduce blood flow across a thickness of the mesh 202. Although FIGS. 2A and 2B depict a device 200 comprising a single mesh 202, in some embodiments, the device 200 comprises multiple occlusive devices (e.g., stents, braids, etc.). A second occlusive can be positioned radially within the mesh 202, radially over the mesh 202, across the mesh 202, and/or end-to-end with the mesh 202. For example, a device of the present technology may comprise a first tubular mesh positioned radially within a second tubular mesh such that the device comprises a combined porosity that is less than a porosity of either the first or second meshes. In some embodiments, a device of the present technology device can comprise a mesh configured to divert blood flow and a stent configured to provide structural support for the mesh. Additional occluding devices can be formed integrally with or independently of the mesh.

According to some embodiments, for example as shown in FIG. 2A, the mesh 202 comprises an entire length and/or circumference of the device. However, the mesh 202 may comprise only a portion of the length and/or circumference of the device 200, for example, when combined with a second occlusive device. In some embodiments, a length of the mesh 202 is based at least in part on a length of an aneurysm neck to be treated. In some embodiments, properties of the mesh 202 (e.g., porosity, thickness, material properties) can be the same throughout the entire device. However, the properties of the mesh 202 may also be varied throughout the device 200. For example, an expandable device of the present technology may comprise one portion configured to be positioned adjacent to the neck of the aneurysm and comprising a low porosity mesh and other portions configured to anchor to a vessel wall and having greater porosity than the porosity of the mesh.

FIG. 2A shows the device 200 in a radially constrained state configured for delivery. In the radially constrained state, the device 200 may comprise a generally tubular shape. The device 200 can comprise a first end portion 204, a second end portion 206, and a longitudinal axis L extending between the first and second end portions 204, 206. In some embodiments, the first end portion 204 is a distal end portion and the second end portion 206 is a proximal end portion. The device may comprise an outer surface, an inner surface, a thickness between the inner and outer surfaces, and a lumen defined by the inner surface and extending from the first end portion 204 to the second end portion 206. One or more ends of the device may be open (i.e., the lumen extends through the end(s) of the device).

According to some embodiments, a diameter and/or a length of the device 200 in the tubular configuration can be based at least in part on anatomy to be treated. For example, in some cases it may be beneficial to select a diameter of the device 200 to be slightly greater than a diameter of the vessel the device is configured to be positioned within. Oversizing the diameter of the device 200 may promote anchoring of the device 200 to the vessel wall. In some embodiments, the diameter of the device 200 varies along a length of the device 200. For example, the first end portion 204 and/or the second end portion 206 can taper in a distal direction or a proximal direction. Alternatively, or in addition, the first end portion 204 and/or the second end portion 206 may flare in a distal direction or a proximal direction. In some embodiments, the diameter of the device 200 is generally constant along a length of the device 200. According to some embodiments, a length of the device can be configured based on a length of a parent vessel, a length of a branching vessel, an angle between two vessels, a length of an aneurysm neck, etc. In some embodiments, the device 200 does not comprise a tubular shape in the radially constrained state. The device 200 can comprise any suitable hollow shape including, but not limited to, round, ovular, elliptical, rectangular, prismatic, etc.

According to some embodiments, the second end portion 206 of the mesh 202 can comprise one or more articulating portions movable relative to the first end portion 204 of the mesh 202. The articulating portions may be separated by one or more slits. For example, as shown in FIG. 2A, the second end portion 206 of the mesh 202 can comprise circumferentially discontinuous first and second articulating portions 208a, 208b (collectively "articulating portions 208"). The articulating portions 208 can be separated by first and second slits 210. Each articulating portion 208 can comprise edges 212 formed by the slits (e.g., longitudinal edges 212a, 212b). According to some embodiments, the number of articulating portions is directly proportional to the number of slits. For example, two slits can form two articulating portions, three slits can form three articulating portions, four slits can form four articulating portions, etc. In some embodiments, the number of slits is greater or less than the number of articulating portions.

In some embodiments, for example as depicted in FIG. 2A, the slits 210 extend along a longitudinal axis L of the device 200. The slits 210 may also extend along a circumference of the device and/or along a direction oblique to the longitudinal and/or circumferential directions. Each of the slits 210 can have a first end, a second end, and a length therebetween. The first and/or second ends of one of the slits 210 can be generally longitudinally aligned with the first and/or second ends of the other slit(s), respectively. In some embodiments, the first ends of the slits 210 are longitudinally offset. In some embodiments, the second ends of the slits 210 are longitudinally offset. The slits 210 may comprise the same length. In some embodiments, the first slit 210a has a length different from or the same as a length of the second slit 210b. As shown in FIGS. 2A and 2B, in some embodiments, the slits 210 extend through a terminus of the device 200. The slits may extend through one, both, or none of the termini of the device 200.

Each of the slits 210 can have a width that defines an opening between an edge 212 of the first articulating portion 208a and a corresponding edge 212 of the second articulating portion 208b adjacent to the slit. In some embodiments, for example as shown in FIG. 2A, the slit width is negligible such that the adjacent edges 212 of first and second articulating portions are disconnected but contact when the device 200 is in the tubular configuration. The slit width can be greater than zero such that the edges 212 of adjacent first and second articulating portions are disconnected and spaced apart by at least the width of the slit.

According to some embodiments, a device of the present technology can be configured to assume an expanded state in which articulating portions are positioned at desired angles to a body portion of the device. For example, FIG. 2B depicts the device 200 in an expanded configuration. In the expanded configuration, the first articulating portion 208a and the second articulating portion 208b can diverge from one another. The first articulating portion 208a (e.g., a longitudinal axis of the first articulating portion 208a) may be positioned at a first angle θ1 to a longitudinal axis of the device L. As shown in FIG. 2B, the first angle may be approximately zero such that the first articulating portion 208a is generally parallel to the longitudinal axis L. The second articulating portion 208b may be positioned at a second angle θ to the longitudinal axis of the device L. In some embodiments, the second angle θ is between about 30 degrees and about 150 degrees. In some embodiments, the first angle is substantially non-zero such that the first articulating portion 208a is not generally parallel with the first end portion 204. The first angle may be between about 30 degrees and about 270 degrees. According to some embodiments, the first angle and/or the second angle θ is between about 90 degrees and about 120 degrees.

Figure 3:
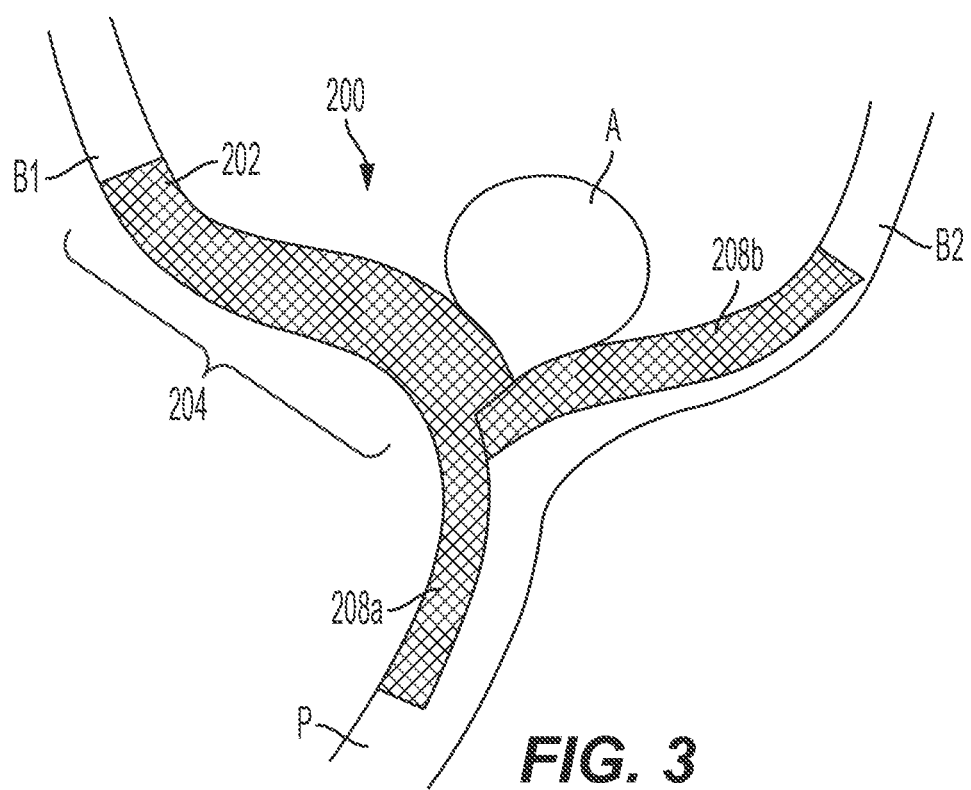
FIG. 3 shows an expandable device in an expanded configuration and positioned at a blood vessel bifurcation configured in accordance with embodiments of the present technology.

Each of the first end portion 204, first articulating portion 208a, and second articulating portion 208b may be configured to be positioned within a lumen of a blood vessel at a bifurcation aneurysm treatment site, as shown in FIG. 3. The first end portion 204 can be configured to be positioned within a lumen of the first branching blood vessel B1. The device 200 can be expanded into a fully expanded configuration (FIG. 3) in which the second articulating portion 208b is positioned within the second branching blood vessel B2 and the first articulating portion 208a is expanded within the parent blood vessel P. As shown in FIG. 3, the first end portion 204 and/or the second articulation portion 208b can be configured to be positioned across the neck of the aneurysm A. The flow-diverting properties these portions of the mesh 202 can be configured to block blood flow into the aneurysm. In some embodiments, any single portion of the device 200 or multiple portions of the device 200 can be configured to be positioned across the neck of the aneurysm.

Each portion (e.g., first end portion 204, first articulating portion 208a, second articulating portion 208b) of the device 200 can be configured to anchor to a blood vessel wall. The extent of anchorage can be based at least in part on a surface area of the portion contacting the vessel wall, a radial force exerted on the vessel wall by the portion, a diameter of the portion relative to a diameter of the vessel wall, a material of the portion, etc. For example, the tubular first end portion 204 may contact an entire circumference of the wall of the first branching blood vessel B1. In contrast, the circumferentially discontinuous second articulating portion 208b may contact only a portion of the circumference of the wall of the second branching blood vessel B2 and, therefore, may anchor to the second branching blood vessel B2 to a lesser extent than the first end portion 204 anchors to the first branching blood vessel B1.

Figure 4B:
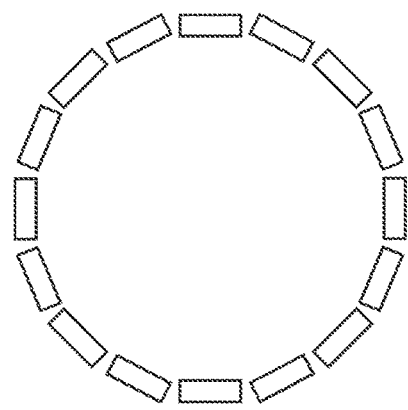
FIG. 4B is an axial cross-sectional view of the expandable device shown in FIG. 4A taken along line 4B-4B.
Figure 4C:
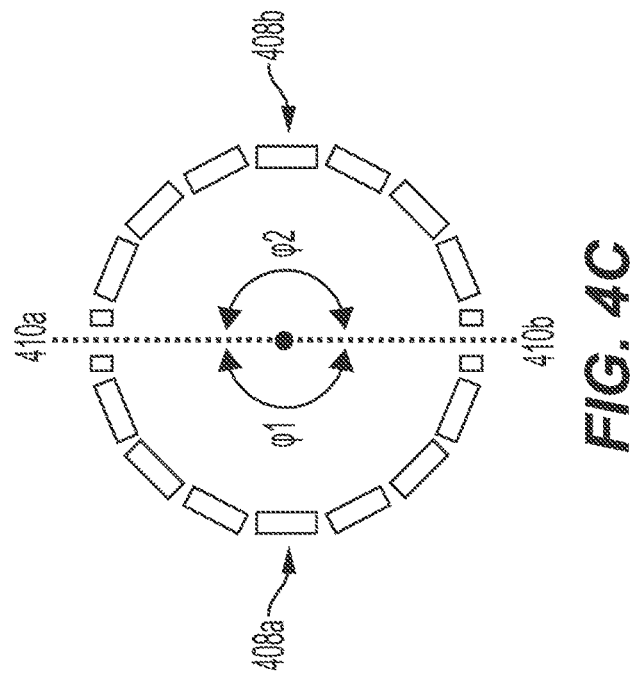
FIG. 4C is an axial cross-sectional view of the expandable device shown in FIG. 4A taken along line 4C-4C.
Figure 4A:
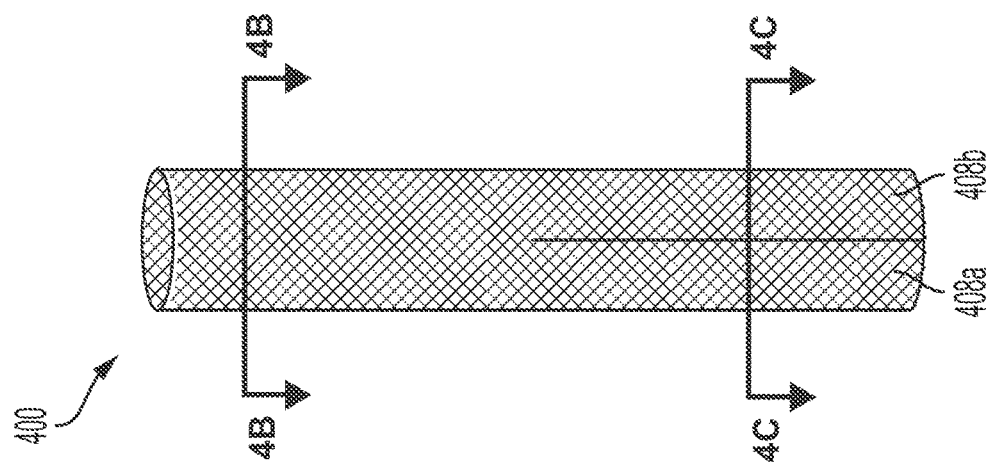
FIG. 4A is an isometric view of an expandable device configured in accordance with embodiments of the present technology.

One or more portions of a device of the present technology can be circumferentially discontinuous to enable the device to anchor to each vessel at a bifurcation, sufficiently cover the neck of the aneurysm, and permit minimally disrupted blood flow from the parent blood vessel to both branching blood vessels, as depicted in FIG. 3. Each of the articulating portions can have a width defined by the angle that the articulating portion subtends, which may be based on radial spacing of the slits separating adjacent articulating portions. For example, FIG. 4A depicts a device 400 with first and second articulating portions 408a, 408b separated by first and second slits 410a, 401b extending along a longitudinal axis of the device. FIG. 4B shows an axial cross-sectional view of the first end portion 404 of the mesh taken along line 4B-4B. As shown in FIG. 4B, an axial cross-sectional shape of the circumferentially continuous first end portion 404 is a complete circle. The circumferentially discontinuous first and second articulating portions 408a, 408b can each have an axial cross-sectional shape of an arc that subtends an angle (see FIG. 4C). For example, as shown in FIG. 4C, the first articulating portion 408a subtends a first angle φ1 and the second articulating portion 408b subtends a second angle φ2. The first and second slits 410a, 410b are spaced apart by about 180 degrees, therefore, both φ1 and φ2 are equal to about 180 degrees and the first and second articulating portions 408a, 408b comprise approximately equivalent widths (and subtended angles).

In some embodiments, the articulating portions subtend different angles and comprise different widths. For example, FIGS. 5A and 5B show isometric and cross-sectional views, respectively, of a device 500 with a first articulating portion 508a subtending a first angle φ1 and a second articulating portion 508b subtending a second angle φ2 that is greater than φ1. In some embodiments, the magnitude of angles φ1 and φ2 can be based on radial spacing of slits 510. In embodiments in which a device comprises more than two articulating portions, some or all of the articulating portions may comprise the same width. In some embodiments, some or all of the articulating portions may comprise different widths. A width of an articulating portion may be selected based on an intended position of the articulating portion at a treatment site. For example, in some embodiments it may be advantageous for an articulating portion configured to be positioned at least partially across an aneurysm neck to have a larger width to ensure complete coverage of the aneurysm neck.

An expandable device in accordance with the present technology can have any suitable number of articulating portions. For example, the device 600 depicted in FIGS. 6A and 6B comprises a tubular first end portion 604 and one articulating portion 608 extending from the first end portion 604. The circumferentially discontinuous articulating portion 608 can subtend an angle as previously described. In some embodiments, the articulating portion 608 subtends an angle of about 180 degrees to form a half tubular shape, as shown in FIGS. 6A and 6B. According to some embodiments, the articulating portion 608 subtends an angle between about 10 degrees and about 350 degrees, between about 20 degrees and about 340 degrees, between about 20 degrees and about 330 degrees, between about 30 degrees and about 320 degrees, between about 40 degrees and about 310 degrees, between about 50 degrees and about 300 degrees, between about 60 degrees and about 290 degrees, between about 70 degrees and about 280 degrees, between about 80 degrees and about 270 degrees, between about 90 degrees and about 260 degrees, between about 100 degrees and about 250 degrees, between about 110 degrees and about 240 degrees, between about 120 degrees and about 230 degrees, between about 130 degrees and about 220 degrees, between about 140 degrees and about 210 degrees, between about 150 degrees and about 200 degrees, or between about 160 degrees and about 190 degrees.

When the device 600 is in the radially constrained state, as shown in FIG. 6A, a longitudinal axis of the articulating portion 608 may be generally parallel to a longitudinal axis L of the device 600. In the expanded state, the articulating portion 608 may be configured such that the longitudinal axis of the articulating portion 608 is positioned at an angle θ relative to the longitudinal axis L of the device 600. According to some embodiments, the device 600 may be configured to be positioned across an aneurysm between branching vessels, between a parent vessel and a first branching vessel, and/or between a parent vessel and a second branching vessel. The angle θ between the longitudinal axis L of the device 600 and the articulating portion 608 may be based in part on the treatment site. For example, the first end portion 604 may be configured to be positioned within a first branching vessel and the articulating portion 608 may be configured to be positioned within a second branching vessel and the angle θ may be based on an angle between the first and second branching vessels. In some embodiments, the angle θ is between about 30 degrees and about 270 degrees. According to some embodiments, the angle θ is between about 90 degrees and about 120 degrees.

Figure 7B:
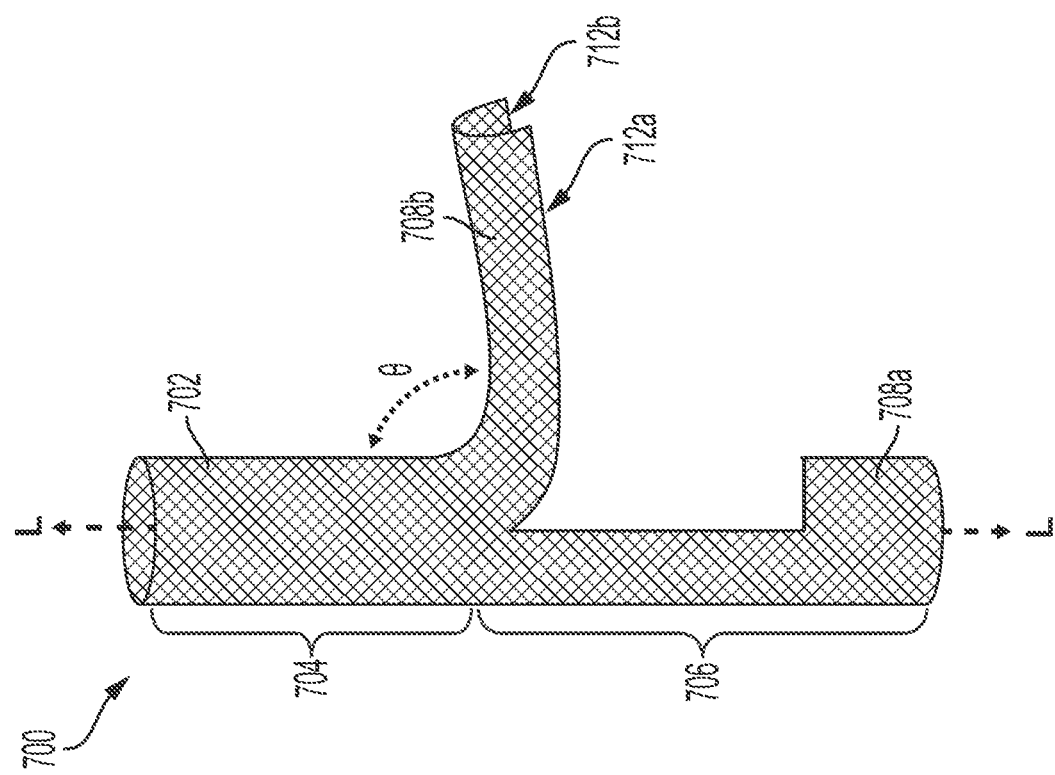
FIGS. 7A and 7B are isometric views of an expandable device configured in accordance with embodiments of the present technology, shown in a tubular configuration and an expanded configuration, respectively.
Figure 7A:
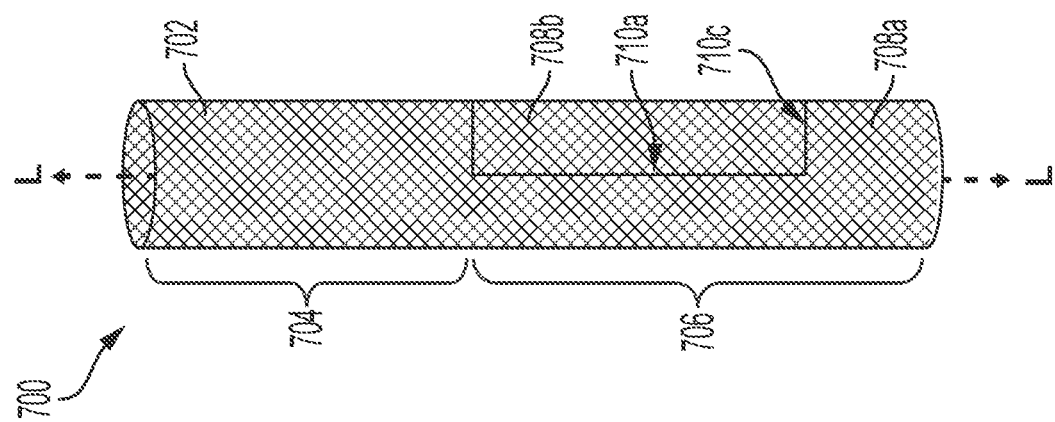

According to some embodiments, for example as shown in FIG. 7A, a device 700 of the present technology can comprise a mesh 702 having a tubular first end portion 704 and a second end portion 706 comprising a first articulating portion 708a and a second articulating portion 708b. The first articulating portion 708a can comprise a circumferentially discontinuous portion, as previously described, and circumferentially continuous tubular portion. In some embodiments, the tubular first end portion is a distal end portion configured to be positioned within a first branching blood vessel and the tubular portion of the first articulating portion 708a is a proximal portion configured to be positioned within a parent blood vessel. The second articulating portion 708b may comprise three edges that are disconnected from the first articulating portion 708a by three slits 710. As shown in FIG. 7A, two slits 710a, 710b can extend longitudinally and one slit 710c can extend circumferentially between the two longitudinal slits 710a, 710b. The two longitudinal slits 710a, 710b may extend along only a portion of the second end portion 706 and do not extend through a terminus of the device 700. The second articulating portion can subtend an angle of about 180 degrees, as shown in FIGS. 7A and 7B. In some embodiments, the second articulating portion 708b can subtend an angle between about 10 degrees and about 350 degrees, as previously described. In the expanded configuration (FIG. 7B), the first articulating portion 708a can be configured to be generally parallel to the first end portion 704 or the first articulating portion 708a can be configured to be positioned at a non-zero first angle relative to the first end portion 704. The second articulating portion 708b may be positioned at a second angle θ relative to the first end portion 704 in the expanded configuration. As previously described, the angle θ may be between about 30 degrees and about 270 degrees. According to some embodiments, the angle θ is between about 90 degrees and about 120 degrees.

Figure 8:
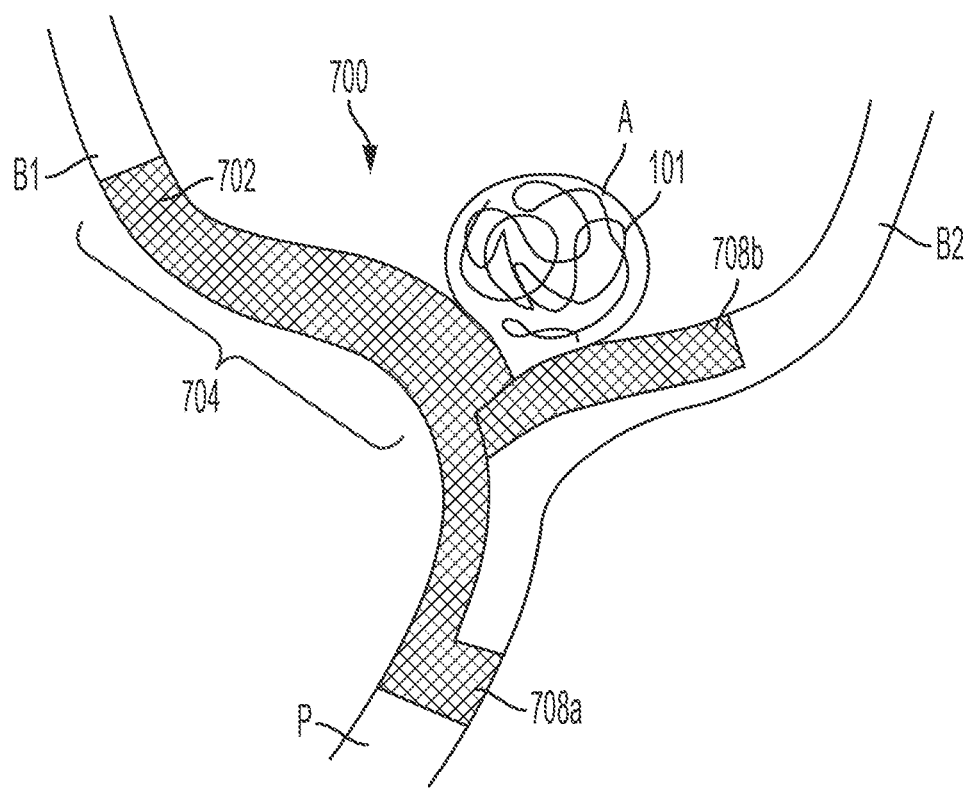
FIG. 8 shows an expandable device in an expanded configuration and positioned at a blood vessel bifurcation configured in accordance with embodiments of the present technology and an example intrasaccular occlusive device positioned within an aneurysm.

According to some embodiments, for example as shown in FIG. 8, an expandable, flow-diverting device of the present technology, such as device 700, may be used with additional occlusive devices to treat the aneurysm A. Embolic coils 101 may be placed within the aneurysm prior to deployment of the device 700 at the treatment site. In the expanded configuration, at least one portion of the device 700 (e.g., first end portion 704 and second articulating portion 708b in FIG. 8) is configured to be positioned across the neck of the aneurysm. The portion(s) of the device 700 covering the neck of the aneurysm may prevents the embolic coils 101 from prolapsing out of the aneurysm and into the branching and/or parent blood vessels. The occlusive device may be any suitable occlusive device such as embolic coils, liquid embolics, braids, etc.

Figure 9:
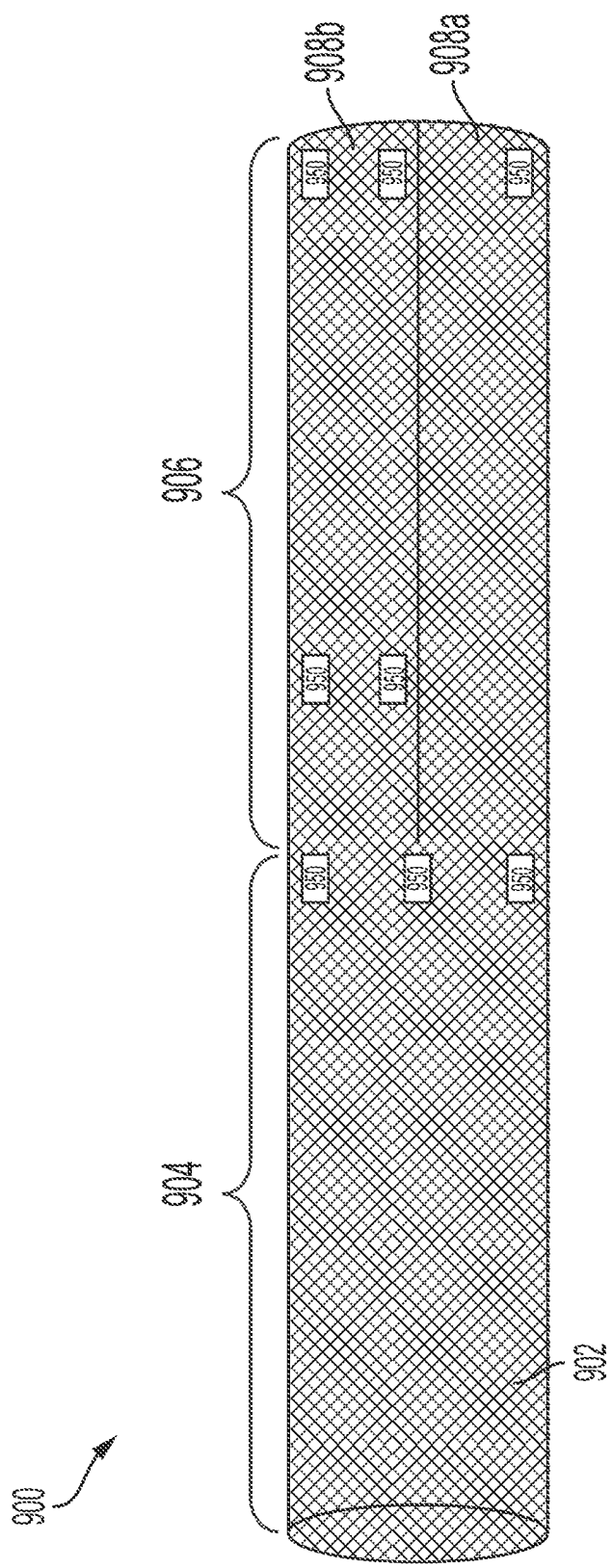
FIG. 9 is an isometric view of an expandable device shown in a tubular configuration and configured in accordance with embodiments of the present technology.

An expandable device of the present technology, such as device 900 shown in FIG. 9, can comprise a radiopaque material (e.g., platinum, platinum-iridium, tantalum, gold, tungsten) to improve visualization of the device 900 within a patient's vasculature. For example, the device 900 can comprise one or more radiopaque markers 950 that can be attached to the mesh 902. The radiopaque markers 950 can comprise coils, bands, plated material, etc. The radiopaque markers 950 may be permanently coupled the device 900 by welding, mechanical attachment, adhesive, or another suitable joining method. In some embodiments, the radiopaque markers are detachably coupled to the device 900. The radiopaque markers may be disposed on an outer surface of the device 900, an inner surface of the device 900, and/or between the inner and outer surfaces of the device 900. In some embodiments, one or more portions of the mesh 902 of the device 900 (e.g., one or more mesh struts, one or more mesh wires) are formed of the radiopaque material.

As illustrated in FIG. 9, the radiopaque markers 950 can be attached to the device 900 in a specific pattern to visualize and/or distinguish certain portions of the device. For example, radiopaque markers 950 may be attached to the device 900 in a longitudinal region that is adjacent a second end portion 906 of the device 900. Multiple radiopaque markers 950 may be attached around a circumference of the device 900 in the longitudinal region. The radiopaque markers 950 may be evenly or unevenly spaced around the circumference of the device 900. In addition, or alternatively, the radiopaque markers 950 can be attached to articulating portion(s) 908. When the device 900 comprises multiple articulating portions 908, one articulating portion 908 may comprise a greater number of radiopaque markers 950 than the other articulating portion 908 and/or a different arrangement of radiopaque markers 950 to facilitate identification of the articulating portions 908 when the device 900 is within the patient's vasculature. For example, the first articulating portion 908a shown in FIG. 9 comprises one radiopaque marker, whereas the second articulating portion 908b comprises four radiopaque markers. Radiopaque markers 950 may be spaced circumferentially around each of the articulating portions 908. Although FIG. 9 shows eight radiopaque markers, any suitable number and distribution of radiopaque markers 950 can be used. In various embodiments, the distribution of radiopaque markers 950 along the device 900 can be circumferentially asymmetric, such that the first and second articulating portions 908a and 908b can be distinguished from one another under fluoroscopy.

The expandable devices disclosed herein can be manufactured using any suitable techniques or materials. Forming an expandable device of the present technology may include obtaining an expandable mesh formed from one or more metals, polymers, composites, and/or biologic materials. In some embodiments, the expandable mesh may be formed from metal(s) or alloy(s) including superelastic metals/alloys (e.g., nickel-titanium alloys such as Nitinol, etc.) or other metals/alloys such as stainless steel, cobalt-chromium alloys, cobalt-nickel alloys (e.g., 35N LT™ available from Fort Wayne Metals of Fort Wayne, Ind. USA), etc., and be configured to self-expand when released from a delivery catheter as described elsewhere herein. In some embodiments, the expandable mesh can be formed from platinum, platinum-tungsten alloy, gold, magnesium, iridium, chromium, zinc, titanium, tantalum, and/or alloys of any of the foregoing metals or including any combination of the foregoing metals. In several embodiments, the expandable mesh may be highly polished and/or surface treated to further improve hemocompatibility. The expandable mesh may be constructed solely from metallic materials without the inclusion of any polymer materials or may include a combination of polymer and metallic materials. Some or all of the expandable mesh may be formed at least in part from radiopaque material, metal or alloy.

In some embodiments, some or all of the mesh may be formed of strands or wires that have been braided or woven together. The strands may have a bi-component (or multi-component) configuration comprising an inner core material surrounded by an outer shell material. The core material may include any of the materials disclosed in the preceding paragraph, and the outer material may include any of the materials disclosed in the preceding paragraph. In some embodiments, the core material may be different than the outer material. For example, in some embodiments, the core material is a radiopaque material (e.g., platinum, platinum-tungsten alloy, tantalum, gold, tungsten, etc., or generally one that is more radiopaque than the outer material), and the outer material is a resilient or highly elastic and/or super-elastic material (e.g., Nitinol, 35N LT, etc., or generally one that is of higher Young's modulus than the outer material). The core material may have a cross-sectional area (based on a cross-sectional dimension $d_c$) that comprises about 5% to about 50%, about 10% to about 45%, about 15% to about 40%, about 10%, about 15%, about 20%, about 25%, about 30%, about 35%, about 40%, about 45% of the total-cross-sectional area of the individual strands (this measure is referred to as the "percent fill" of the strand 18 accounted for by the core material 22).

Some suitable materials and combinations for the strands of the expandable mesh include: (a) all strands of coaxial bi-component configuration, with a cobalt-nickel outer material and a platinum or platinum-tungsten (or other radiopaque) core material; (b) all strands of coaxial bi-component configuration, with a nickel-titanium outer material and a platinum or platinum-tungsten (or other radiopaque) core material; (c) a combination of some coaxial bi-component strands of cobalt-nickel outer material and a platinum or platinum-tungsten (or other radiopaque) core material, and some single-component strands of cobalt-nickel; (d) a combination of some coaxial bi-component strands of nickel-titanium outer material and a platinum or platinum-tungsten (or other radiopaque) core material, and some single-component strands of nickel-titanium; (e) a combination of some single-component strands of cobalt-nickel or nickel-titanium with some single-component strands of platinum or platinum-tungsten (or other radiopaque material).

In some embodiments, the mesh may be formed from sheet or tube of any suitable material such as, but not limited to, the materials described elsewhere herein. Any suitable cutting process such as cutting, laser cutting, milling, chemical etching, wire electrical discharge machining (EDM), water jetting, punching (stamping), chemical etching, etc. may be used to cut the mesh from the material. The sheet or tube of material can have a thickness selected to achieve the desired material properties of the resulting mesh. In various embodiments, the thickness of the sheet or tube of material can be uniform or can vary (e.g., along a gradient, being thinned at particular regions using etching, grinding, etc., or thickened at particular regions using deposition, etc.). In some embodiments, the mesh is formed directly as a sheet or tube by an additive process such as thin film deposition, 3D printing, etc.

In some embodiments, the mesh can be bent or otherwise manipulated to create the tubular configuration of the mesh (e.g., the radially constrained configuration). For example, in embodiments in which the mesh is initially formed of a flat sheet of material (e.g., by laser cutting a sheet, by thin film deposition, etc.), the tubular configuration can be created by removably coupling the mesh to a tubular mold or fixture and subjecting the mesh to a heat treatment process, as described elsewhere herein. In some embodiments, the tubular configuration is formed by deforming the flat sheet of material into a generally tube-like shape such that the longitudinal edges of the flat pattern are positioned adjacent to or in contact with one another. The longitudinal edges can be joined (e.g., via laser welding) along all or a portion of their respective lengths. In some embodiments, the edges can overlap so that the overlapping portion comprises two radial layers of the mesh.

Articulating portions of the present technology can be formed by creating slits in the mesh. In some embodiments, the slits can be formed by a suitable cutting process such as, but not limited to, the cutting processes previously described. The cut edges of the mesh can be secured by welding, crimping, melting, gluing, braiding, clamping, or another suitable securing method. In some embodiments, various portions of the mesh (e.g., first end portion, articulating portions) can be formed separately and then coupled together. The portions of the mesh can be coupled by any suitable joining method such as, but not limited to, welding, crimping, melting, gluing, etc. In some embodiments, an articulating portion can be formed by extruding a material forming the first end portion of the mesh.

In some embodiments, the mesh can be bent or otherwise manipulated via a shape setting process to create the expanded configuration of the mesh in which one or more articulating portions are positioned at an angle to a first end portion of the device. In some embodiments, the shape set process comprises manipulating the mesh into the intended expanded configuration (e.g., by coupling to a mold or fixture) and subjecting the mesh to a heat treatment. One example, of a heat treatment procedure can include heating the mesh to a selected temperature for a selected period of time, followed by rapid cooling. The rapid cooling can be achieved by any suitable cooling procedure such as, but not limited to water quench or air-cooling. In particular examples, the heat treatment procedure may be carried out in an air or vacuum furnace, salt bath, fluidized sand bed or other suitable system. In other examples, other suitable heat-treating procedures may be employed including, but not limited to, resistive heating or heating by running a current though the metal of the appliance structure. One or more additional post processing operations may be provided on the mesh after preliminary shape setting, including, but not limited to, abrasive grit blasting, shot peening, polishing, chemical etching, electropolishing, electroplating, coating, ultrasonic cleansing, sterilizing or other cleaning or decontamination procedures.

In some embodiments, a single shape-setting step may be completed to deform the mesh to its desired expanded configuration. However, in certain embodiments the shape setting may include two or more shape-setting steps (e.g., two or more heat treatment processes, potentially using two or more different fixtures). In such cases, the amount of deformation imparted to the mesh within each shape-setting step may be limited, with each subsequent shape-setting step moving the mesh further toward the desired expanded configuration.

The present disclosure also includes methods of treating a vascular condition, such as an aneurysm, with any of the embodiments of the expandable devices disclosed herein. The expandable device may be deployed across the neck of an aneurysm and its flow-diverting properties employed to reduce blood flow between the aneurysm and the parent vessel, cause the blood inside the aneurysm to thrombose, and/or lead to healing of the aneurysm.

Figure 10:
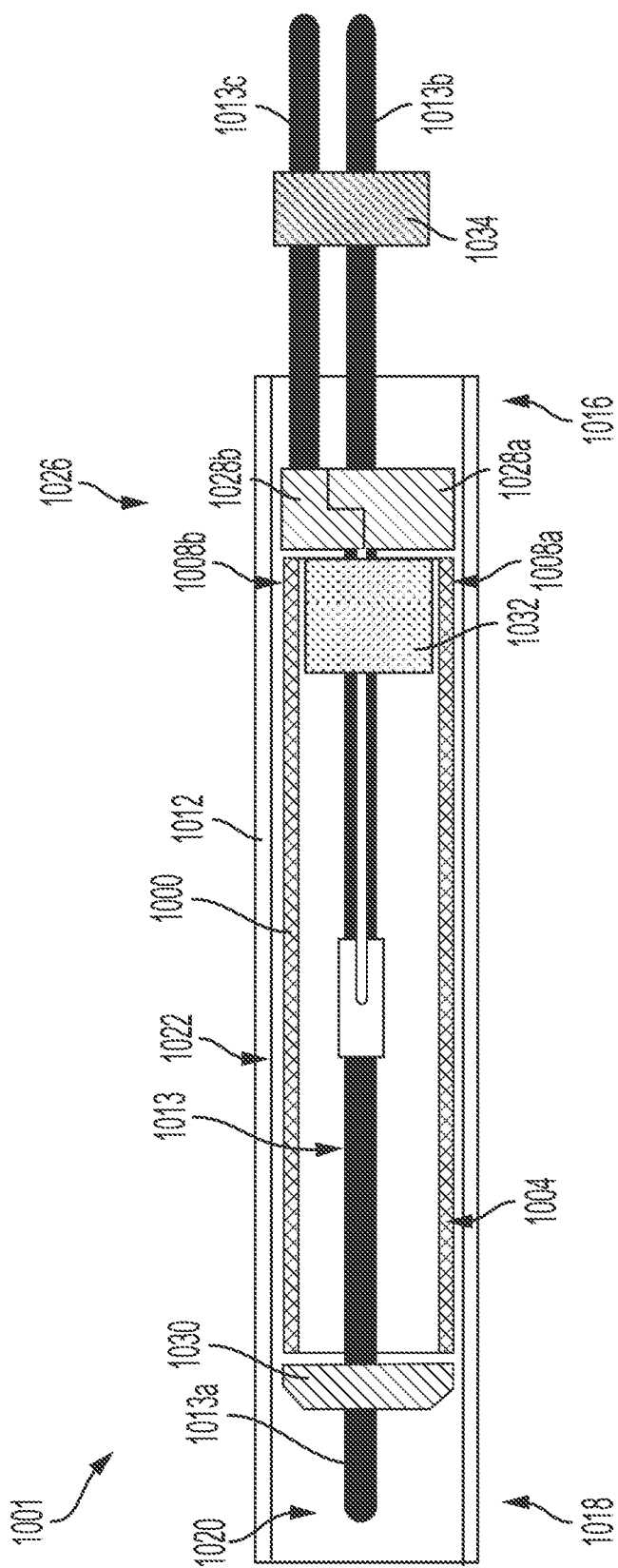
FIG. 10 is a schematic side view of a delivery system of the present technology.

FIG. 10 shows a side view of an example of a delivery system 1001 in accordance with the present technology. The delivery system may comprise an elongate tube 1012 (e.g., a microcatheter) having a proximal end portion 1016, a distal end portion 1018, a lumen 1020 extending from the proximal end portion 1016 to the distal end portion 1018, and an inner surface 1022 defining the lumen 1020. At the distal end portion 1018, the elongate tube 1012 may be open. The elongate tube 1012 may be configured to slidably receive a core member 1013 configured to carry an expandable device 1000. The core member 1013 may be configured to be advanced beyond the distal portion 1018 to expand or deploy the expandable device 1000 within a blood vessel. In operation, the core member 1013 may be distally advanced relative to the tube 1012, or the tube 1012 may be proximally retracted relative to the core member 1013. The elongate tube 1012 can define a generally longitudinal dimension extending between the proximal end portion 1016 and the distal end portion 1018. When the delivery system 1001 is in use, the longitudinal dimension need not be straight along some or any of its length.

The core member 1013 may comprise a distal portion 1013a configured to extend generally longitudinally through the lumen of the elongate tube 1012. The core member 1013 may further comprise a first proximal portion 1013b and a second proximal portion 1013c. The first and second proximal portions 1013b, 1013c may be radially spaced apart, as shown in FIG. 10. The first proximal portion 1013b may be configured to move the entire expandable device 1000 and/or a first articulating portion of the expandable device 1000 through the elongate tube 1012, whereas the second proximal portion 1013c may be configured to move and/or deploy a second articulating portion 1008b of the expandable device 1000. The core member 1013 can generally comprise any member(s) with sufficient flexibility and column strength to move the expandable device 1000 through the elongate tube 1012. The core member 1013 can therefore comprise a wire, tube (e.g., hypotube), braid, coil, or other suitable member(s), or a combination of wire(s), tube(s), braid(s), coil(s), etc.

The delivery system 1001 can also include a coupling assembly 1026 or resheathing assembly 1026 configured to releasably retain the expandable device 1000 with respect to the core member 1013. The coupling assembly 1026 can be configured to engage the expandable device 1000, via abutment of the proximal end or edge of the expandable device 1000, mechanical interlock with the pores and filaments of the expandable device 1000, frictional engagement with the inner wall of the expandable device 1000, any combination of these modes of action, or another suitable mode of action. The coupling assembly 1026 can therefore cooperate with the inner surface 1022 of the elongate tube 1012 to grip and/or abut the expandable device 1000 such that the coupling assembly 1026 can move the expandable device 1000 along and within the elongate tube 1012, e.g., distal and/or proximal movement of the core members 1013 relative to the elongate tube 1012 results in a corresponding distal and/or proximal movement of the expandable device 1000 within the elongate tube lumen 1020.

In some embodiments, the coupling assembly 1026 can comprise one or more proximal restraints 1028 and a distal restraint 1030. The proximal and distal restraints 1028, 1030 can be fixed to the core member(s) 1013 to prevent or limit proximal or distal movement of the coupling assembly 1026 along the longitudinal dimension of the core member 1013. For example, the proximal and distal restraints 1028, 1030 can be soldered or fixed with adhesive to the core member(s) 1013. In some embodiments, as described in further detail below, the proximal restraint 1028 can be sized to abut the proximal end of the expandable device 1000 and be employed to push the device distally during delivery. The distal restraint 1030 can taper in the distal direction down towards the core member 1013. This tapering can reduce the risk of the distal restraint 1030 contacting an inner surface of the expandable device 1000, particularly during navigation of tortuous vasculature, in which the system 1001 can assume a highly curved configuration.

As depicted in FIG. 10, the proximal restraint 1028 may be configured to abut the proximal end or proximal edge of the expandable device 1000. The proximal restraint 1028 may comprise a first portion 1028a fixed to the first proximal portion 1013b of the core member 1013 and a second portion 1028b fixed to the second proximal portion 1013c of the core member 1013. The second portion 1028b of the proximal restraint may be movable relative to the first portion 1028a of the proximal restraint. The first portion 1028a of the proximal restraint 1028 can be configured to abut a first articulating portion 1008a of the expandable device 1000 and the second portion 1028b of the proximal restraint 1028 can be configured to abut a second articulating portion 1008b of the expandable device 1000. In this arrangement each portion of the proximal restraint 1028 can be used to move (e.g., push) the corresponding articulating portion of the expandable device 1000. A push force can be applied to the first proximal portion 1013b of the core member 1013 such that the first portion 1028a of the proximal restraint 1028 abuts the first articulating portion 1008a of the expandable device 1000 and moves the entire expandable device 1000 or only the first articulating portion 1008a distally through the elongate tube 1012. A push force can be applied to the second proximal portion 1013c of the core member 1013 such that the second portion 1028b of the proximal restraint 1028 abuts the second articulating portion 1008b of the expandable device 1000 and moves the second articulating portion 1008b distally through the elongate tube 1012.

The coupling assembly 1026 can also include a resheathing member 1032 positioned about the core member 1013 between the proximal and distal restraints 1028, 1030. The resheathing member 1032 can be a rigid plate, sprocket, pad, or other suitable member with a central aperture configured to receive the core member 1013 therethrough. The resheathing member 1032 may be configured to frictionally engage, mechanically interlock with or otherwise engage the expandable device 1000 such that the resheathing member 1032 restrains the expandable device 1000 from moving longitudinally with respect to the core member 1013. One or more spacers (not shown) can be disposed about the core member 1013 between the resheathing member and the proximal restraints 1028, the distal restraint 1030, and/or additional resheathing members 1032 to define a relative longitudinal positioning between the components on either end of the spacer. The spacer can comprise a wire coil, a solid tube, or other structural element that can be mounted over the core member 1013. In some embodiments, the spacer can be a zero-pitch coil with flattened ends. In some embodiments, the spacer can be a solid tube (e.g., a laser-cut tube) that can be rotatably mounted or non-rotatably fixed (e.g., soldered) to the core member 1013. The spacers can have a radially outermost dimension that is smaller than a radially outermost dimension of the resheathing member 1032 such that the spacer does not contact the expandable device 1000 during normal operation of the system 1001. Although the embodiment illustrated in FIG. 10 includes one resheathing member 1032 and no spacers, the number of resheathing members and spacers can vary. In at least one embodiment, the coupling assembly 1026 includes only a single resheathing member 1032 without any spacers. In other embodiments, the number of resheathing members can vary, for example two, three, four, five, six, or more resheathing members separated by spacers.

When the proximal restraint 1028 is configured to push the expandable device 1000 distally, the proximal restraint accordingly transmits some, most, or all of the distal longitudinal (push) force to the expandable device 1000, wholly or partially in place of the resheathing member(s) 1032. In such a configuration, the resheathing members 1032 can transmit little or no push force to the expandable device 1000 while the expandable device 1000 is delivered distally along the length of the elongate tube 1012. Advantageously, this reduces or eliminates the tendency of the resheathing member(s) 1032 to distort pores of the expandable device 1000. Use of the proximal restraint 1028 to move the expandable device 1000 in this manner can also reduce or eliminate longitudinal movement of the expandable device 1000 relative to the core members 1013 that sometimes accompanies the pore distortion described above. In most cases, the vast majority of the travel of the expandable device 1000 within the elongate tube 1012 is in the distal or "push" direction during delivery to the treatment location, in contrast to the relatively short travel involved in resheathing the expandable device 1000, in the proximal or "pull" direction. Therefore, configuring the proximal restraint 1028 to transmit most or all of the push force to the expandable device 1000 can significantly reduce or substantially eliminate such distortion and/or relative longitudinal movement of the stent.

The coupling assembly 1026 of FIG. 10 can therefore employ the proximal restraint 1028 as a pushing element to transmit at least some, or most or all, distally directed push force to the expandable device 1000 during delivery. In such a coupling assembly 1026, the resheathing member(s) 1032 do not transmit any distally directed push force to the expandable device 1000 during delivery (or transmit only a small portion of such force, or do so only intermittently). The resheathing member(s) 1032 can transmit proximally-directed pull force to the expandable device 1000 during retraction or resheathing, and the proximal restraint 1028 can transmit no proximally directed pull force to the stent (or it may do so occasionally or intermittently, for example when a portion of the expandable device 1000 becomes trapped between the outer edge of the proximal restraint 1028 and the inner wall of the elongate tube 1012).

In some embodiments, the resheathing member(s) 1032 are employed for both distal and proximal movement of the expandable device 1000 with respect to the elongate tube 1012. The resheathing member(s) 1032 can transmit distally directed force to the expandable device 1000 to move it distally within the elongate tube 1012 during delivery, and proximally directed force to the expandable device 1000 to move it proximally into the elongate tube 1012 during resheathing. In such embodiments, the proximal restraint 1028 can be made with a relatively small outer diameter, and/or be positioned sufficiently proximal of the proximal end of the expandable device 1000, to prevent the proximal restraint 1028 from transmitting distally directed push forces to the expandable device 1000 during delivery.

The resheathing members 1032 can be fixed to the core member 1013 so as to be immovable relative to the core member 1013, in a longitudinal/sliding manner and/or in a radial/rotational manner. Alternatively, the resheathing members 1032 can be coupled to (e.g., mounted on) the core member 1013 so that the resheathing members 1032 can rotate about the longitudinal axis of the core member 1013, and/or move or slide longitudinally along the core member 1013. In such embodiments, the resheathing members 1032 can each have an inner lumen or aperture that receives the core member 1013 therein such that the resheathing members 1032 can slide and/or rotate relative to the core member 1013.

In some embodiments, the resheathing members 1032 can be mounted onto the core member 1013 to permit not only rotational movement but also a degree of tilting of the resheathing members 1032 with respect to a longitudinal axis of the core member 1013. For example, the holes in the resheathing members 1032 can be larger than the outer diameter of the corresponding portion of the core member 1013, thereby permitting both rotational movement and tilting with respect to the core member 1013. "Tilting" as used herein means that the long axis of the resheathing member 1032 (i.e., an axis extending along the longest dimension of the resheathing member 1032, substantially parallel to the proximal-facing and distal-facing end faces of the resheathing member 1032) is non-orthogonal to a longitudinal axis of the core member 1013. For example, in one tilted configuration, the long axis of the resheathing member 1032 can intersect the core member 1013 at approximately 85 degrees, indicating 5 degrees of tilt. Depending on the dimensions of the resheathing members 1032 and the core member 1013, the degree of tilting permitted can vary. In some embodiments, one or both of the resheathing members 1032 can tilt with respect to the core member 1013 by 30 degrees or less, 20 degrees or less, 10 degrees or less, or 5 degrees or less. In some embodiments, one or both of the resheathing members 1032 can tilt with respect to the core member by at least 5 degrees, by at least 10 degrees, by at least 20 degrees, or more.

Proper positioning of an expandable device of the present technology requires an articulating portion to be oriented adjacent to the vessel it is intended to be expanded into. The delivery system 1001 can comprise an orientation member 1034 to facilitate proper rotation of the expandable device 1000 during delivery. The orientation member 1034 can be coupled to the first and/or second proximal portions 1013*a*, 1013*b* of the core member 1013. In some embodiments, the orientation member 1034 is fixed to the first proximal portion 1013*b* of the core member 1013 and is slidable over the second proximal portion 1013*c* of the core member 1013. As a result, the first and second proximal portions 1013*b* and 1013*c* can be slidably moved relative to one another.

In operation, the expandable device 1000 can be moved distally or proximally within the elongate tube 1012 via the core member 1013 and the coupling assembly 1026. To move the expandable device 1000 out of the elongate tube 1012, either one or both proximal portions of the core member 1013 are moved distally while the elongate tube 1012 is held stationary or the one or more proximal portions of the core member 1013 are held stationary while the elongate tube 1012 is withdrawn proximally. When the proximal portion(s) of the core member 1013 are moved distally, the distal face of the proximal restraint 1028 bears against the proximal end of the expandable device 1000 and causes the expandable device to be advanced distally, and ultimately out of the distal portion 1018 of the elongate tube 1012. In embodiments wherein the resheathing member(s) 1032 are employed to transmit pushing force to the expandable device 1000, the mechanical engagement or interlock between the resheathing member 1032 and the expandable device 1000, in response to the application of a distally directed force to the core member 1013, causes the expandable device 1000 to move distally through and out of the elongate tube 1012. Conversely, to resheath or otherwise move the expandable device 1000 into the elongate tube 1012, the relative movement between the core member 1013 and the elongate tube 1012 is reversed compared to moving the expandable device 1000 out of the elongate tube such that the proximal region of the distal restraint 1030 bears against the distal end of the expandable device and thereby causes the resheathing member 1032 to be retracted relative to the elongate tube 1012. The mechanical engagement between the resheathing member 1032 and the expandable device 1000 may accordingly hold the expandable device 1000 with respect to the core member 1013 such that proximal movement of the expandable device 1000 relative to the elongate tube 1012 enables resheathing of the expandable device 1000 back into the distal portion 1018 of the elongate tube 1012. This can be useful when the expandable device 1000 has been partially deployed and a portion of the expandable device 1000 remains disposed between at least one resheathing member 1032 and the inner surface 1022 of the elongate tube 1012 because the expandable device 1000 can be withdrawn back into the distal opening of the elongate tube 1012 by moving the core member 1013 proximally relative to the elongate tube 1012 (and/or moving the elongate tube 1012 distally relative to the core member 1013). Resheathing in this manner remains possible until the resheathing member 1032 and/or elongate tube 1012 have been moved to a point where the resheathing member 1032 is beyond the distal opening of the elongate tube 1012 and the expandable device 1000 is released from between the resheathing member 1032 and the elongate tube 1012.

In some embodiments, delivering an expandable device of the present technology can begin with obtaining percutaneous access to the patient's arterial system, typically via a major blood vessel in a leg or arm. A guidewire can be placed through the percutaneous access point and advanced to the treatment location, which can be in an intracranial artery, or any neurovascular artery, peripheral artery, or coronary artery. The elongate tube 1012 (e.g., a microcatheter) can be advanced over the guidewire to a treatment site having an aneurysm at a vessel bifurcation. The distal portion 1018 of the elongate tube 1012 can be advanced into the first branching vessel. The guidewire can then be withdrawn from the elongate tube 1012 and the core member 1013 and core assembly 1026, together with the expandable device 1000 mounted thereon or supported thereby, can be advanced through the elongate tube 1012 to the distal portion 1018 of the elongate tube 1012. Radiopaque markers of the expandable device 1000 can be visualized with fluoroscopy to identify the orientation and/or position of the expandable device 1000 at the treatment site. The orientation member 1034 can be used to rotate the expandable device 1000 within the elongate tube 1012 and/or within the vessel to achieve the proper rotational orientation. A first (e.g., distal) end portion 1004 of the expandable device 1000 can be expanded within the first branching vessel as previously described by applying a push force to the first proximal portion 1013b of the core member 1013. The expandable device 1000 may self-expand into apposition with the inner wall of the first branching blood vessel. In some embodiments, an additional expansion device (e.g., balloon, energy source) can be used to facilitate or cause expansion of the device 1000. In some embodiments, once the first end portion 1004 of the expandable device 1000 is deployed, the second articulating portion 1008b may be deployed into the second branching blood vessel. A force can be applied to the second proximal portion 1013c of the core member 1013 to cause the second portion 1028b of the proximal restraint 1028 to move the second articulating portion 1008b into the second branching blood vessel. For example, the second portion 1028b of the proximal restraint 1028 can be distally advanced relative to the first portion 1028a. By virtue of this distal advancement, the second portion 1028b of the proximal restraint can urge the second articulating portion 1008b radially outwardly. The second articulating portion 1008b can expand into apposition with the inner wall of the second branching blood vessel so that at least a portion of the first end portion 1004 and/or the second articulating portion 1008b is positioned across the neck of an aneurysm between the first and second branching blood vessels. The first articulating portion 1008a may be advanced out of the elongate tube 1012 and expanded into apposition with the inner wall of the parent blood vessel. The delivery system 1001 can be removed from the patient, leaving the implanted expandable device 1000 positioned within the parent and branching vessels and across the neck of the bifurcation aneurysm.

CONCLUSION

Although many of the embodiments are described above with respect to systems, devices, and methods for treating cerebral aneurysms, the technology is applicable to other applications and/or other approaches, such as pulmonary or cardiac applications. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1A-10.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

The invention claimed is:

1. An implantable device configured to be positioned across a neck of an aneurysm at a bifurcation of a blood vessel of a patient to prevent or limit blood flow into the aneurysm, the device comprising:
   a generally tubular mesh configured to be implanted within the blood vessel, the mesh having a constrained state for a delivery through a catheter and an expanded state, wherein the tubular mesh comprises a circumferentially continuous first end portion configured to be positioned within a first lumen of the blood vessel and a second end portion, the second end portion comprising (i) a circumferentially discontinuous first articulating region comprising a first surface concave towards a longitudinal dimension of the tubular mesh, a first longitudinal edge, and a second longitudinal edge, opposite the first longitudinal edge along a width of the first articulating region, the first articulating region being configured to be positioned within a second lumen of the blood vessel and (ii) a partially circumferentially discontinuous second articulating region comprising a circumferentially discontinuous portion extending away from the first end portion to a circumferentially continuous portion, the circumferentially discontinuous portion comprising a second surface concave towards the longitudinal dimension of the tubular mesh, opposite the first surface along a circumference of the tubular mesh, a third longitudinal edge, and a fourth longitudinal edge opposite the third longitudinal edge along a width of the second articulating region, the second articulating region being configured to be positioned within a third lumen of the blood vessel, wherein the first and second lumens are distal of the third lumen,
   a first plurality of radiopaque markers attached to the first articulating region and a second plurality of radiopaque markers attached to the second articulating region, wherein the first plurality of radiopaque markers comprises fewer radiopaque markers than the second plurality of radiopaque markers,
   wherein in the constrained state the first longitudinal edge of the first articulating region is located adjacent to the third longitudinal edge of the second articulating region and the second longitudinal edge of the first articulating region is located adjacent to the fourth longitudinal edge of the second articulating region such that the second end portion of the mesh is substantially tubular and the first surface of the first articulating region and the second surface of the second articulating region define a lumen of the second end portion,
   wherein in the expanded state, the tubular mesh is configured so that the first articulating region is positionable at a first angle relative to the first end portion and the second articulating region is positionable at a second angle relative to the first end portion such that the first longitudinal edge of the first articulating region forms a third angle, greater than 90 degrees, with the third longitudinal edge of the second articulating region so that the first articulating region and the second articulating region are extendable in opposite directions in the second lumen of the blood vessel and the third lumen of the blood vessel, respectively, with at least a portion of the mesh proximate to a connection between the first end portion and the first articulating region being positioned across the neck of the aneurysm in order to prevent or limit blood flow into the aneurysm.

2. The device of claim 1, wherein a length of the first articulating region is less than a length of the second articulating region.

3. The device of claim 1, wherein the first longitudinal edge of the first articulating region is circumferentially spaced apart from the second longitudinal edge of the first articulating region by about 180 degrees.

4. The device of claim 1, wherein a width of the first articulating region is less than the width of the second articulating region.

5. The device of claim 1, wherein the first angle is about 0 degrees and the second angle is between about 30 degrees and 150 degrees.

6. The device of claim 1, wherein the first angle is substantially equivalent to the second angle.

7. The device of claim 1, wherein longitudinal edges of the first and second articulating regions have been soldered, melted, welded, or glued.

8. The device of claim 1, wherein in the constrained state, the first longitudinal edge of the first articulating region is spaced apart from the third longitudinal edge of the second articulating region by a first gap and the second longitudinal edge of the first articulating region is spaced apart from the fourth longitudinal edge of the second articulating region by a second gap.

9. The device of claim 1, further comprising a plurality of radiopaque markers positioned around a circumference of the first end portion of the mesh.

10. An implantable device configured to be positioned across a neck of an aneurysm at a bifurcation of a parent blood vessel of a patient into a first branching blood vessel and a second branching blood vessel to prevent or limit blood flow into the aneurysm, the device comprising:
   an expandable mesh configured to be implanted within the first branching blood vessel and the second branching blood vessel, the expandable mesh having a low-profile configuration for a delivery through a catheter and an expanded configuration, wherein the expandable mesh comprises a generally tubular body portion extending from a first end to a second end along a longitudinal dimension of the body portion and an arm portion comprising a circumferentially discontinuous region and a circumferentially continuous region, the circumferentially discontinuous region comprising a surface concave towards the longitudinal dimension of the tubular body portion and extending from a first end at the first end of the body portion to a second end at the circumferentially continuous region along a longitudinal dimension of the arm portion, wherein the body portion carries a plurality of first radiopaque markers spaced apart around a circumference of the body portion and the arm portion carries at least one second radiopaque marker,
   wherein in the low-profile configuration, the longitudinal dimension of the arm portion is generally parallel with the longitudinal dimension of the body portion, and
   wherein in the expanded configuration, the expandable mesh is configured so that the longitudinal dimension of the arm portion is positionable at an angle with respect to the longitudinal dimension of the body portion so that the body portion is configured to be positioned within a lumen of the first branching blood vessel and the arm portion is configured to be positioned within a lumen of the second branching blood vessel such that the first end of the body portion and the first end of the arm portion are positioned proximal of the second end of the body portion and the second end of the arm portion and the expandable mesh is positioned across the neck of the aneurysm, the aneurysm being located between the first and second branching blood vessels, in order to prevent or limit blood flow into the aneurysm.

11. The device of claim 10, wherein the angle is between about 30 degrees and about 150 degrees.

12. The device of claim 10, wherein the arm portion is a first arm portion, the arm portion further comprising a second arm portion extending from the body portion, wherein, when the expandable mesh is in an expanded configuration, the longitudinal dimension of the first arm portion is positioned at a first angle to the longitudinal dimension of the body portion and a longitudinal dimension of the second arm portion is positioned at a second angle to the longitudinal dimension of the body portion.

13. The device of claim 12, wherein the second arm portion is configured to be positioned within a lumen of a parent blood vessel, the parent blood vessel being located proximal of the first and second branching blood vessels.

14. The device of claim 10, wherein the mesh has a sufficiently low porosity such that the mesh is configured to divert blood flow away from the aneurysm.

15. The device of claim 10, wherein the mesh is configured to anchor to a blood vessel wall of the blood vessel of the patient.

16. The device of claim 10, wherein the mesh comprises a braid.

17. The device of claim 10, wherein the mesh is formed of a shape memory alloy.

18. An implantable device for reducing blood flow into a bifurcation aneurysm of a patient, the bifurcation aneurysm being located between two blood vessels at a bifurcation of a parent blood vessel into first and second branching blood vessels, the device comprising:

an expandable mesh configured to be implanted within a vasculature of the patient, the expandable mesh having (i) a radially constrained configuration for a delivery through a catheter in which the expandable mesh is substantially tubular and defines a lumen of the expandable mesh and (ii) an expanded configuration, the expandable mesh comprising a partially circumferentially discontinuous first portion comprising a circumferentially discontinuous first region and a generally tubular second region, the first region comprising a first surface concave towards the lumen of the expandable mesh, a first longitudinal edge, and a second longitudinal edge, opposite the first longitudinal edge along a width of the first portion, the first portion carrying at least one first radiopaque marker, a circumferentially discontinuous second portion comprising a second surface concave towards the lumen of the expandable mesh, a third longitudinal edge, and a fourth longitudinal edge, opposite the third longitudinal edge along a width of the second portion, the second portion carrying at least one second radiopaque marker, and a generally tubular third portion opposite the first portion and the second portion along a length of the expandable mesh, the third portion carrying a plurality of third radiopaque markers spaced apart about a circumference of the third portion, wherein in the radially constrained configuration, the first longitudinal edge of the first region is located adjacent to the third longitudinal edge of the second region and the second longitudinal edge of the first region is located adjacent to the fourth longitudinal edge of the second region such that the expandable mesh comprises a substantially tubular shape, wherein in the expanded configuration, the expandable mesh is configured so that the second portion is positionable at a first angle relative to the first portion substantially corresponding to a first angle between the first branching blood vessel and the parent blood vessel and the third portion is positionable at a second angle relative to the first portion substantially corresponding to a second angle between the second branching blood vessel and the parent blood vessel so that the first portion is configured to be positioned within the parent blood vessel with the generally tubular second region proximal of the circumferentially discontinuous first region, the second portion is configured to be positioned within the first branching blood vessel, and the third portion is configured to be positioned within the second branching blood vessel, such that at least a portion of the expandable mesh is positioned across a neck of the bifurcation aneurysm and the mesh has a sufficiently low porosity to substantially block blood flow across the mesh and into the bifurcation aneurysm while permitting blood flow from the parent blood vessel to the first and second branching blood vessels.

19. The device of claim 18, wherein the circumferentially discontinuous second portion and the third portion are configured to substantially cover the neck of the aneurysm.

20. The device of claim 18, wherein the first and third portions are configured to substantially cover the neck of the aneurysm.

21. The device of claim 18, wherein the first portion and the circumferentially discontinuous second portion are configured to substantially cover the neck of the aneurysm.

22. An implantable device for reducing blood flow into a bifurcation aneurysm within a patient's vasculature, the bifurcation aneurysm being located between two blood vessels at a bifurcation of a parent blood vessel into first and second branching blood vessels, the device comprising:

an expandable mesh configured to be implanted within the patient's vasculature, the expandable mesh having (i) a radially constrained configuration for a delivery through a catheter in which the expandable mesh is substantially tubular and defines a lumen of the expandable mesh and (ii) an expanded configuration, the expandable mesh comprising a first portion comprising a first plurality of radiopaque markers, a second portion comprising a second plurality of radiopaque markers, and a third portion comprising a third plurality of radiopaque markers, wherein the first and third portions are substantially tubular along at least a portion of their respective lengths and the second portion is circumferentially discontinuous, wherein each of the first plurality of radiopaque markers, the second plurality of radiopaque markers, and the third plurality of radiopaque markers are arranged in a specific pattern for distinguishing the first portion, the second portion, and the third portion of the mesh from one another, wherein in the radially constrained configuration, the expandable mesh comprises a substantially tubular shape, and wherein in the expanded configuration, the first portion is configured to be positioned within a lumen of the parent blood vessel, the second portion is positioned within a lumen of the first branching blood vessel, the third portion is positioned within a lumen of the second branching blood vessel, and at least a portion of the expandable mesh is positioned across a neck of the bifurcation aneurysm and has a sufficiently low porosity to substantially block blood flow across the mesh and into the bifurcation aneurysm while permitting substantially unobstructed blood flow from the parent blood vessel to the first and second branching blood vessels.

23. The device claim 22, wherein the second portion subtends an angle of about 30 degrees to about 330 degrees.

* * * * *

UNITED STATES PATENT AND TRADEMARK OFFICE
CERTIFICATE OF CORRECTION

PATENT NO. : 11,633,193 B2
APPLICATION NO. : 16/948127
DATED : April 25, 2023
INVENTOR(S) : Jalgaonkar et al.

It is certified that error appears in the above-identified patent and that said Letters Patent is hereby corrected as shown below:

In the Claims

In Column 27, in Claim 23, Line 14, delete "device" and insert -- device of --, therefor.

Signed and Sealed this
Fifteenth Day of August, 2023

Katherine Kelly Vidal
*Director of the United States Patent and Trademark Office*